US010052299B2

(12) United States Patent
Shchepinov

(10) Patent No.: US 10,052,299 B2
(45) Date of Patent: Aug. 21, 2018

(54) ALLEVIATING OXIDATIVE STRESS DISORDERS WITH PUFA DERIVATIVES

(75) Inventor: Mikhail S. Shchepinov, Oxford (GB)

(73) Assignee: Retrotope, Inc., Los Altos, CA (US)

( * ) Notice: Subject to any disclaimer, the term of this patent is extended or adjusted under 35 U.S.C. 154(b) by 1345 days.

(21) Appl. No.: 12/916,347

(22) Filed: Oct. 29, 2010

(65) Prior Publication Data
US 2011/0105609 A1 May 5, 2011

Related U.S. Application Data

(60) Provisional application No. 61/256,815, filed on Oct. 30, 2009.

(51) Int. Cl.
A61K 31/20 (2006.01)
A61K 31/23 (2006.01)
C07C 57/03 (2006.01)
A61K 31/201 (2006.01)
A61K 31/202 (2006.01)
C07B 59/00 (2006.01)

(52) U.S. Cl.
CPC ............ *A61K 31/20* (2013.01); *A61K 31/201* (2013.01); *A61K 31/202* (2013.01); *C07B 59/001* (2013.01)

(58) Field of Classification Search
USPC ........................................................ 514/549
See application file for complete search history.

(56) References Cited

U.S. PATENT DOCUMENTS

| | | | |
|---|---|---|---|
| 3,520,872 A | 7/1970 | Wechter et al. | |
| 5,194,448 A | 3/1993 | Coupland et al. | |
| 5,436,269 A | 7/1995 | Yazawa | |
| 5,709,888 A | 1/1998 | Gil et al. | |
| 5,843,497 A | 12/1998 | Sundram et al. | |
| 5,914,347 A * | 6/1999 | Grinda | A61K 9/146 514/549 |
| 6,111,066 A | 8/2000 | Anderson et al. | |
| 6,417,233 B1 | 7/2002 | Sears et al. | |
| 6,503,478 B2 | 1/2003 | Chaiken et al. | |
| 2001/0023259 A1 | 9/2001 | Slabas et al. | |
| 2002/0198177 A1 | 12/2002 | Horrobin | |
| 2004/0043013 A1 | 3/2004 | McCleary | |
| 2005/0164908 A1 | 7/2005 | Ginsberg et al. | |
| 2006/0035382 A1 | 2/2006 | Shinozaki et al. | |
| 2006/0205685 A1 | 9/2006 | Phiasivongsa et al. | |
| 2006/0241088 A1 | 10/2006 | Arterburn et al. | |
| 2007/0004639 A1* | 1/2007 | Kane | A61K 31/19 514/183 |
| 2007/0032548 A1 | 2/2007 | Ellis | |
| 2008/0234197 A1* | 9/2008 | Allam et al. | 514/12 |
| 2009/0054504 A1 | 2/2009 | Bozik et al. | |
| 2009/0069354 A1 | 3/2009 | Czarnik | |
| 2009/0182022 A1 | 7/2009 | Rongen et al. | |
| 2009/0215896 A1 | 8/2009 | Morseman et al. | |
| 2009/0232916 A1 | 9/2009 | Shulman et al. | |
| 2009/0306015 A1 | 12/2009 | Gately et al. | |
| 2009/0326070 A1 | 12/2009 | Freeman et al. | |
| 2010/0022645 A1 | 1/2010 | Nelson | |
| 2010/0160248 A1 | 6/2010 | Shchepinov | |
| 2011/0028434 A1 | 2/2011 | Destaillats et al. | |
| 2011/0028493 A1 | 2/2011 | Matsunaga et al. | |
| 2011/0082206 A1 | 4/2011 | Miller | |
| 2011/0190195 A1 | 8/2011 | Atlas | |

FOREIGN PATENT DOCUMENTS

| | | |
|---|---|---|
| CN | 1114878 A | 1/1996 |
| EP | 0713653 A1 | 5/1996 |
| EP | 1548116 | 6/2005 |
| EP | 1834639 A1 | 9/2007 |
| EP | 1961311 A1 | 8/2008 |
| EP | 2641891 A1 | 9/2013 |
| FR | 2721518 | 12/1995 |
| JP | 2-237919 | 9/1990 |
| JP | H8-268885 | 10/1996 |
| JP | H9-143492 | 6/1997 |
| JP | 10-291955 | 11/1998 |
| JP | 2000-290291 | 10/2000 |
| JP | 2001-145880 | 5/2001 |
| JP | 2001-514239 | 9/2001 |
| JP | 2001-270832 | 10/2001 |
| JP | 2001-519355 | 10/2001 |
| JP | 2002-513911 | 5/2002 |
| JP | 2002-527387 | 8/2002 |
| JP | 2004-81156 | 3/2004 |

(Continued)

OTHER PUBLICATIONS

Shcehepinov et al. (Isotope effect, essential diet components, and Prospects of Aging Retardation), Russian Journal of General Chemistry), 2010, vol. 80, No. 7, pp. 1514-1522.*
Brenna, Thomas (Efficiency of conversion of alpha-linoleic acid to long chain n-3 fatty acids in man, 2002 Lippincott Williams a.*
Sumbalova et al., Brain energy metabolism in experimental chronic diabetes: effect of long-term administration of coenzyme Q10 and ω-3 polyunsaturated fatty acids, Biologia Bratislava, 60(17):105-108, 2005.*
Shchepinov, Reactive Oxygen Species, Isotope Effect, Essential Nutrients, and Enhanced Longevity, Rejuvenation Research, 10(1):47-59, 2007, and DiMauro, Mitochondrial Respiratory-Chain Diseases, N Engl J Med, 348:2656-68, 2003.*
Rustin et al., Effect of idebenone on cardiomyopathy in Friedreich's ataxia: a preliminary study, The Lancet, 354:477-479, 1999.*
DiMauro, Mitochondrial Respiratory-Chain Diseases, N Engl J Med, 348:2656-68, 2003.*
Finglas et al, Use of an oral/intravenous dual-label stable-isotope protocol to determine folic acid bioavailability from fortified cereal grain foods in women, The Journal of Nutrition, vol. 132, No. 5, pp. 936-939, May 2002.

(Continued)

Primary Examiner — Jeffrey S Lundgren
Assistant Examiner — Michael J Schmitt
(74) Attorney, Agent, or Firm — Knobbe, Martens, Olson & Bear, LLP

(57) ABSTRACT

Some aspects of the invention provide for essential fatty acids which are substituted in specific positions to slow down oxidative damage by Reactive Oxygen Species (ROS), and to suppress the rate of consequent formation of reactive products, for the purpose of preventing or reducing the damage associated with oxidative stress associated diseases such as neurological diseases and age-related macular degeneration (AMD).

22 Claims, 11 Drawing Sheets

(56) References Cited

FOREIGN PATENT DOCUMENTS

| | | | | |
|---|---|---|---|---|
| JP | 2004-520848 | 7/2004 | | |
| JP | 2004-530635 | 10/2004 | | |
| JP | 2005-510501 | 4/2005 | | |
| JP | 2002-536981 | 11/2005 | | |
| JP | 2006-502081 | 1/2006 | | |
| JP | 2006-504701 | 2/2006 | | |
| JP | 2006-510669 | 3/2006 | | |
| JP | 2008-504372 | 2/2008 | | |
| JP | 2009-007337 | 1/2009 | | |
| JP | 2009-502745 | 1/2009 | | |
| JP | 2009-525948 | 7/2009 | | |
| JP | 2010-521493 | 6/2010 | | |
| JP | 2013-509439 | 3/2013 | | |
| KR | 10-2005-0029582 | 3/2005 | | |
| WO | WO 9956790 | 11/1999 | | |
| WO | WO00/21524 | 4/2000 | | |
| WO | WO01/17374 A1 | 3/2001 | | |
| WO | WO02/096221 | 5/2002 | | |
| WO | WO03/035095 | 5/2003 | | |
| WO | WO2003/051348 | 6/2003 | | |
| WO | WO03/064576 A2 | 8/2003 | | |
| WO | WO2004/028536 | 4/2004 | | |
| WO | WO2004/029254 | 4/2004 | | |
| WO | WO2004/052227 | 6/2004 | | |
| WO | WO2005/037848 A2 | 4/2005 | | |
| WO | WO 2007/049098 | 5/2007 | | |
| WO | WO 2007102030 | 9/2007 | | |
| WO | WO 2007102030 A1 * | 9/2007 | ............... | A23D 9/00 |
| WO | WO2008/143642 A2 | 11/2008 | | |
| WO | WO2009/017833 | 2/2009 | | |
| WO | WO2009/097331 A1 | 8/2009 | | |
| WO | WO2009/123316 | 8/2009 | | |
| WO | WO2009/114809 | 9/2009 | | |
| WO | WO2009/114814 | 9/2009 | | |
| WO | WO2009/151125 A1 | 12/2009 | | |
| WO | WO2010/010365 A1 | 1/2010 | | |
| WO | WO2010/014585 | 2/2010 | | |
| WO | WO2010/068867 | 6/2010 | | |
| WO | WO2010/106211 | 9/2010 | | |
| WO | WO2010/132347 A2 | 11/2010 | | |
| WO | WO2010/143053 A1 | 12/2010 | | |
| WO | WO2011/053870 | 5/2011 | | |
| WO | WO2011/097273 A1 | 8/2011 | | |
| WO | WO2012/148926 | 11/2012 | | |
| WO | WO2012/148927 | 11/2012 | | |
| WO | WO2012/148929 | 11/2012 | | |
| WO | WO2012/148930 | 11/2012 | | |
| WO | WO2012/174262 A2 | 12/2012 | | |

OTHER PUBLICATIONS

Notice of Reasons for Rejection dated Aug. 24, 2011 for Japanese Patent Application No. 2008-557833.
Tucker et al; The synthesis of 11,11-Dideuterolinoleic Acid; Journal of Labelled Compounds; vol. VII, No. 1, Jan.-Mar. 1970.
Brenna et al; High-Precision Continuous-Flow Isotope Ratio Mass Spectrometry; Mass Spectrometry Review; vol. 16; pp. 227-258; 1997.
Brenna et al; α-Linolenic acid supplementation and conversionton to n-3 long-chain polyunsaturated fatty acids in humans; Prostaglandins, Leukotrienes and Essential Fatty Acids; vol. 80; pp. 85-91; 2009.
Brenna, J.T.; Efficiency of conversion of a-linolenic acid to long chain n-3 fatty acids in man; Lipid Metabolism; pp. 127-132; 2002.
Brenna, J.T.; Use of stable isotopes to study fatty acid and lipoprotein metabolism in man; Prostaglandins, Leukotrienes and Essential Fatty Acids; vol. 57 (4 & 5); pp. 467-472; 1997.
Emken et al; Effect of Dietary Docosahexaenoic Acid on Desaturation and Uptake in vivo of Isotope-Labeled Oleic, Linoleic, and Linolenic Acids by Male Subjects; Lipids; vol. 34, No. 8; pp. 785-791; 1999.
Emken et al; Metabolism of cis-12-octadecenoic acid and trans-9, trans-12-octadecadienoic acid and their influence on lipogenic enzyme activities in mouse liver; Biochimica et Biophysica Acta; vol. 919; pp. 111-121; 1987.
Hill et al. Isotope-reinforced polyunsaturated fatty acids protect yeast cells from oxidative stress. Free Radical Biology & Medicine, Jan. 1, 2011, vol. 50, pp. 130-138.
Hill et al; Small amounts of isotope-reinforced polyunsaturated fatty acids suppress lipid autoxidation; Free Radical Biology and Medicine, vol. 53, pp. 893-906; 2012.
Lefkowitz et al; Where Does the Developing Brain Obtain Its Docosahexaenoic Acid? Relative Contributions of Dietary α-Linolenic Acid, Docosahexaenoic Acid, and Body Stores in the Developing Rat; Pediatric Research; vol. 57, No. 1; pp. 157-165; 2005.
Levenson et al; The Healing of Rat Skin Wounds; Annals of Surgery, vol. 161, No. 2; pp. 293-308; Feb. 1965.
Lin et al; Whole body distribution of deuterated linoleic and α-linolenic acids and their metabolites in the rat; Journal of Lipid Research; vol. 48; pp. 2709-2724; 2007.
Rohwedder et al; Measurement of the Metabolic Interconversion of Deuterium-Labeled Fatty Acids by Gas Chromatography/Mass Spectrometry; Lipids; vol. 25, No. 7; pp. 401-405; 1990.
Rosen et al; Effect of Deuterium Oxide on Wound Healing, Collagen and Metabolism of Rats; New England Journal of Medicine; vol. 270, No. 22; pp. 1142-1149; May 28, 1964.
Salem et al; Arachidonic and docosahexaenoic acids are biosynthesized from their 18-carbon precursors in human infants; Proc. Natl. Acad. Sci.; vol. 93; pp. 49-54; Jan. 1996.
Shchepinov et al. Isotope effect, essential diet components, and prospects of aging retardation. Russian Journal of General Chemistry, 2010, vol. 80, No. 7, pp. 1514-1522.
International Search Report and Written Opinion dated Nov. 29, 2012 for PCT/US2012/034832.
International Search Report and Written Opinion dated Nov. 29, 2012 for PCT/US2012/034836.
International Search Report and Written Opinion dated Nov. 29, 2012 for PCT/US2012/034833.
International Search Report and Written Opinion dated Nov. 29, 2012 for PCT/US2012/034835.
Nass et al; Caenorhabditis elegans in Parkinson's Disease Drug Discovery: Addressing an Unmet Medical Need; Molecular Interventions; vol. 8, Issue 6; pp. 284-293; Dec. 2008.
Harman, Denham; Aging and Oxidative Stress; Journal of International Federation of Clinical Chemistry (JIFCC), vol. 10, No. 1; pp. 24-26; Mar. 1998.
Harman, Deham; The Free Radical Theory of Aging; Antioxidants & Redox Signaling; vol. 5, No. 5, pp. 557-561, Oct. 2003.
Hulme et al; Chemistry and the Worm: *Caenorhabditis elegans* as a Platform for Integrating Chemical and Biological Research; Chemical Biology; Angewandte Chemie International Edition; vol. 50; pp. 4774-4807, 2011.
Dalle-Donne et al; Protein carbonylation in human diseases; Trends in Molecular Medicine; Apr. 2003, vol. 9, No. 4, pp. 169-176.
Demidov, V.; Heavy isotopes to avert ageing?; Trends in Biotechnology; Aug. 2007, vol. 25, No. 9, pp. 371-375.
International Search Report and Written Opinion dated Dec. 23, 2010 for PCT/US10/54866.
International Search Report dated Jun. 12, 2007 for PCT/GB2007/050112.
Kelly et al; Assessing the authenticity of single seed vegetable oils using fatty acid stable carbon isotope ratios (13C/12C); Food Chemistry; 1997; vol. 59, No. 2, pp. 181-186; Elsevier Science Ltd.
Knapp et al; Temperature-dependent isotope effects in soybean lipoxygenase-I : Correlating hydrogen tunneling with protein dynamics; JACS Articles; J. Am. Chem. Soc.; vol. 124; pp. 3865-3874; published online Mar. 20, 2002.
Kushner et al; Pharmacological uses and perspectives of heavy water and deuterated compounds; Canadian Journal of Physiology and Pharmacology; Feb. 1999; vol. 77, pp. 79-88.
Rapoport et al; Delivery and turnover of plasma-derived essential PUFAs in mammalian brain; Journal of Lipid Research; May 2001; vol. 42; pp. 678-685.

(56) References Cited

OTHER PUBLICATIONS

Shchepinov, Mikhail; Reactive Oxygen Species, Isotope Effect, Essential Nutrients, and Enhanced Longevity; Rejuvenation Research; 2007; vol. 10, No. 1, pp. 47-59.
Wade, David; Deuterium isotope effects on noncovalent interactions between molecules; Chemico-Biological Interactions; 1999; vol. 117, No. 3, pp. 191-217.
Written Opinion dated Sep. 8, 2008 for PCT/GB2007/050112.
S.C. Barber et al., Biochimica et Biophysica Acta 1762 (2006) 1051-1067.
Simpson et al., Neurology. May 25, 2004;62(10):1758-65.
Pedersen et al., Annals of Neurology (Nov. 1998), vol. 44, Issue 5, pp. 819-824.
Mitsumoto et al., Amyotroph Lateral Scler. (2008); 9(3): 177-183.
Yashodhara et. al., Postgrad Med J (2009) 85: 84-90.
Reddy P. H., Neuromolecular Med. (2008) 10(4): 291-315.
Veldink et al., J Neuro Neurosvrg Psychiatry. (2007) 78:367-371.
Shchepinov et al., Mitigating effects of oxidation in aging and diseases. Retrotope. 2010; 1-11.
Triglycerides. Medium chain triglycerides. Alternative Medicine Review. 2002; 7(5): 418-420.
Nelson et al., "Reduction of beta-Amyloid Levels by Novel Protein Kinase C epsilon Activators", Journal of Biological Chemistry, vol. 284, No. 50, Dec. 2009, pp. 34514-34521.
Extended European Search Report for European Application No. 12776294 dated Sep. 25, 2014 by European Patent Office.
Nobuo Tamiya and Takehiko Shimanouchi; Infra-red absorption spectra of deuterated aspartic acids; Spectrochimica Acta, vol. 18, No. 7, pp. 895-905; Jul. 1, 1962.
Office Action for U.S. Appl. No. 14/551,450 dated Apr. 15, 2015 by U.S. Patent and Trademark Office.
Wendt et al., Mass spectrometry of perdeuterated molecules of biological origin fatty acid esters from Scenedesmus obliquus. Biochemistry. 1970;9 (25): 4854-4866.
Asada et al; Stereochemistry of meso-α,ω Diaminopimelate Decarboxylase Reaction: The First Evidence for Pyriodoxal 5'-Phosphate Dependant Decarboxylation with Inversion of Configuration, Biochemistry, 1981, vol. 20, No. 24, pp. 6881-6886.
Bada et al; Isotopic Fractionation During Peptide Bond Hydrolysis, Geochimica et Cosmoschimica Acta, 1989, vol. 53, pp. 3337-3341.
Balasubramanian et al; DNA strand breaking by the hydroxyl radical is governed by the accessible surface areas of the hydrogen atoms of the DNA backbone. Proc. Natl. Acad. Sci. USA, Aug. 1998, vol. 95 pp. 9738-9743.
Brandl et al; The biosynthesis of 3-(trans-2-Nitrocyclopropyl)alanine, a Constituent of the Signal Metabolite Hormaomycin; European Journal of Organic Chemistry, published online Dec. 20, 2004, vol. 2005, No. 1, pp. 123-135.
Burdzy et al; Synthesis of stable-isotope enriched 5-methylpyrimidines and their use as probes of base reactivity in DNA, Nucleic Acids Research, 2002, vol. 30, No. 18, pp. 4068-4074.
Chen et al., One-Pot Selective Deuteriation of 5'-Dimethoxytritylated Deoxynucleotide Derivatives; Bioorgainc & Medicinal Chemistry Letters, vol. 4, No. 6, pp. 789-794, 1994.
Chiriac et al; Synthesis of [1,3,6,7-15N, 8-13C] adenine; Journal of Labelled Compounds and Radiopharmaceuticals; Apr. 1999 (published online May 4, 1999); vol. 42, issue 4, pp. 377-385.
Cho et al; Cooperativity and anti-cooperativity between ligand binding and the dimerization of ristocetin A: asymmetry of a homodimer complex and implications for signal transduction; Chemistry & Biology; Mar. 1996; vol. 3, issue 3, pp. 207-215.
Esaki et al; Synthesis of base-selectively deuterium-labelled nucleosides by the Pd/C-Catalyzed H-D Exchange Reaction in Deuterium Oxide; Heterocycles; 2005; vol. 66, pp. 361-369.
Foldesi et al; The Synthesis of Deuterionucleosides; Nucleosides, Nucleotides and Nucleic Acids; 2000, vol. 19, No. 10-12, pp. 1615-1656.

Geboes et al, Validation of a new test meal for a protein digestion breath test in humans, The Journal of Nutrition, vol. 134, No. 4, pp. 806-810, Apr. 2004.
Ikeya et al; Evaluation of stereo-array isotope labeling (SAIL) patterns for automated structural analysis of proteins with CYANA, Magnetic Resonance in Chemistry, Jul. 2006, vol. 44, spec. No. S152-S157.
Kelland et al; Stereochemistry of Lysine Formation by meso-Diaminopimelate Decarboxylase from Wheat Germ: Use of 1H-13C NMR Shift Correlation to Detect Stereospecific Deuterium Labeling, Biochemistry, Jun. 1985, vol. 24, No. 13, pp. 3263-2367.
Kishore et al; Partial 13C Isotopic Enrichment of Nucleoside Monophosphates: Useful Reporters for NMR Structural Studies; Nucleic Acids Research; Oct. 2005, vol. 33, No. 18.
Lichtenstein et al; Comparison of deuterated leucine, valine and lysine in the measurement of human apolipoprotein A-I and B-100 kinetics; Journal of Lipid Research; 1990; vol. 31, No. 9, pp. 1693-1702.
Oba et al; A simple rout to L-[5,5,6,6-D4] lysine starting from L-pyroglutamic acid, Japanese Journal of Deuterium Science, 2006, vol. 12, No. 1, pp. 1-5.
Raap et al; Enantioseletive syntheses of isotopically labeled a-amino acids. Preparation of (ε-13C)-L-α-aminoadipic acid and five isotopomers of L-lysine with 13C, 15N, and 2H in the δ- and ε-positions; Recueil de Travaux Chimiques de Pays-Bas, 1990, vol. 109, No. 4, pp. 277-286.
Ren et al; Simultaneous metabolic labeling of cells with multiple amino acids: localization and dynamics of histone acetylation and methylation, Proteomics: Clinical Applications; Jan. 2007; vol. 1, No. 1, pp. 130-142.
Scholl et al; Synthesis of 5,5,6,6-D4-L-lystine-aflatoxin B1 for use as a mass spectrometric internal standard; Journal of Labelled Compounds & Radiopharmaceuticals; Oct. 2004; vol. 47, No. 11, pp. 807-815.
Svedruzic et al; The Mechanism of Target Base Attack in DNA Cytosine Carbon 5 Methylation; Biochemistry; Aug. 2004; vol. 43, No. 36, pp. 11460-11473.
Tang et al; Kinetic and biochemical analysis of the mechanism of action of lysine 5, 6-aminomutase; Archives of Biochemistry and Biophysics; Oct. 2003; vol. 418, No. 1, pp. 49-54.
The Aldrich Catalog Handbook of Fine Chemicals 2003-2004, p. 141, catalog No. 48, 998-0.
Toyama et al; Assignments and hydrogen bond sensitivities of UV resonance Raman bands of the C8-deuterated guanine ring; Journal of Raman Spectroscopy; Sep. 2002; vol. 33, issue 9, pp. 699-708.
Wheeler et al., The Synthesis of the 2H, 3H, and 14C-Isotopomers of 2'-Deoxy-2', 2'Difourocytidine Hydrochloride, and Anti-Tumor Compound; Journal of Labelled Compounds and Radiopharmaceuticals; vol. XXIX, No. 5., 1991.
Townend et al., "Dietary Macronutrient Intake and Five-year Incident Cataract: The Blue Mountains Eye Study", American Journal of Ophthalmology, Elsevier, Amsterdam, NL, vol. 143, No. 6, May 22, 2007, pp. 932-939.
The extended European search report for European Patent Application No. 12776521 dated Sep. 17, 2014.
Clarke et al., Isotope-reinforced polyunsaturated fatty acids protect yeast cells from oxidative stress. FASEB J. 2010;24:849.2.
Wilczynska-Kwiatek A et al., "Asthma, allergy, mood disorders, and nutrition", European Journal of Medical research, Biomed Central Ltd. London, UK, vol. 14, No. Suppl 4, Dec. 7, 2009, pp. 248-254.
Serhiyenko V et al., "Simvastatin and Omega-Polyunsaturated Fatty Acids in the Treatment of Cardiomyopathy in Type 2 Diabetes Mellitus Patients", Atherosclerosis Supplements, Elsevier, Amsterdam, NL, vol. 9, No. 1, May 1, 2008, p. 203.
The extended European search report for European Patent Application No. 12776313 dated Sep. 17, 2014.
Lambert D. Rationale and applications of lipids as prodrug carriers. European Journal of Pharmaceutical Sciences. 2000;11 (Suppl.2): S 15-S27.
Hepatocellular. Hepatocellular carcinoma. Medscape Reference. 2014;1-5.
Lei et al., Dietary omega-3 Polyunsaturated Fatty Acids Enhance Adiponectin Expression and Protect Against Pressure Overload-

(56) References Cited

OTHER PUBLICATIONS

Induced Left Ventricular Hypertrophy and Dysfunction, Journal of Cardial Failure, Churchill Livingstone, Naperville, IL, US, vol. 13m No. 6, Aug. 1, 2007, p. S79.
Extended European Search Report for European Application No. 12777440 dated Sep. 17, 2014 by European Patent Office.
Neurochem. Res., 2007, vol. 32, pp. 2184-2193.
IOVS, 2003, vol. 44, No. 8, pp. 3663-3668.
The American Journal of Human Genetics, May 15, 2009, vol. 84, pp. 558-566.
Free Radical Biology & Medicine, Oct. 16, 20008, vol. 44, pp. 1259-1272.
Journal of Gastroenterology and Hepatology, 2002, vol. 17, Suppl., pp. S186-S190.
Japanese Journal of Clinical Medicine (Separate Volume) Syndrome classified as New Fields Series 13 Liver/Biliary Tract-based Syndrome (second edition) I Liver edition (the first volume) Sep. 20, 2010 p. 196 to 201.
Separate Volume/Advances in Medical Science Oxidative Stress Ver.2 Oct. 5, 2006, p. 23 to 27.
Giordano, F. J., The Journal of Clinical Investigation , Mar., 2005, vol. 115, No. 3 , p. 500-508.
Keiji Yoneya, et al., Japanese Journal of Clinical Medicine , Oct. 1, 1998 , vol. 56, No. 10 p. 51-56(2509-2514).
Journal of Biliary Tract & Pancreas , 2005, vol. 26, No. 4 , p. 351-357.
Dentistry Dictionary reduced-size edition. Oct. 10, 1989 , the first edition , p. 2216-2217.
Office Action for Japanese Patent Application No. 2014-508488 dated Dec. 4, 2015.
Office Action for Japanese Patent Application No. 2014-508487 dated Dec. 3, 2015.
Ovide-Bordeaux et al., Dicisahexaeniuc acid affects insulin deficiency-and insulin resistance-induced alterations in cardiac mitochondria, Am J Physiol Regul Interg Comp Physiol 286: R519-R527, 2004.
Office Action for Japanese Patent Application No. 2014-508489 dated Dec. 25, 2015.
Office Action for Japanese Patent Application No. 2014-508486 dated Dec. 25, 2015.
Adhikary et al., UVA-visible photo-excitation of guanine radical cations produces sugar radicals in DNA and model structures, Nucleic Acids Research, 2005, vol. 33, No. 17, pp. 5553-5564.
Viswanathan and Cushley, Deuterium Nuclear Magnetic Resonance Study of the Interaction of Substrates and Inhibitors with Soybean Lipoxygenase, The Journal of Biological Chemistry, vol. 256, No. 14, pp. 7155-7160, Issue of Jul. 1981.
Yamauchi et al., Observation of the Pathway from Lysine to Isoprenoidal Lipid of Halophilic Archaea, Halobacterium halobium and Natrinema pallidum, Using Regiospecifically Deuterated Lysine, Bull. Chem. Soc. Jpn., vol. 74, pp. 2199-2205 (2001).
Hill et al., Small amounts of isotope-reinforced polyunsaturated fatty acids suppress lipid autoxidation, Free Radical Biology and Medicine 53 (2012) 893-906.
Zesiewicz et al., Randomized, Clinical Trial of RT001: Early Signals of Efficacy in Friedreich's Ataxia, Published online Apr. 6, 2018 in Wiley Online Library (wileyonlinelibrary.com). DOI: 10.1002/mds.27353.

Adams et al., Case Report: Expanded Access Treatment of an Infantile Neuroaxonal Dystrophy (INAD) Patient with a Novel, Stabilized Polyunsaturated Fatty Acid Drug, American Academy of Neurology conference, poster session, Apr. 2018.
Elharram et al., Deuterium-reinforced polyunsaturated fatty acids improve cognition in a mouse model of sporadic Alzheimer's disease, The FEBS Journal (2017) p. 1-13.
Shchepinov et al., Isotopic reinforcement of essential polyunsaturated fatty acids diminishes nigrostriatal degeneration in a mouse model of Parkinson's disease, Toxicology Letters 207 (2011) 97-103.
Shah et al., Resolving the Role of Lipoxygenases in the Initiation and Execution of Ferroptosis, ACS Cent. Sci., 2018, 4 (3), pp. 387-396; online publication Feb 7, 2018.
Crombie et al, *Synthesis of $[14,14-^2H_2]$-linolenic acid and its use to confirm the pathway to 12-oxophytodienoic acid (12-oxoPDA) in plants: a conspectus of the epoxycarbonium ion derived family of metabolites from linoleic and linolenic acid hydroperoxides*, Journal of the Chemical Society, Perkin Transactions 1, No. 3, Jan. 1991, pp. 581-587.
Dyall et al, *Neurological benefits of Omega-3 Fatty Acids*, Neuromolecular Medicine, vol. 10, No. 4, pp. 219-235, Jun. 10, 2008.
Evans et al, *ENDOR, triple resonance and ESR studies of spin-trapped radicals in autoxidized linoleic acid and its deuterated derivatives*, Biochimica et Biophysica Acta, Elsevier Science BV, Amsterdam, NL, vol. 835, No. 3, pp. 421-425, Jul. 31, 1985.
Hussein, N., *Long-chain conversion of $[^{13}C]$ linoleic acid and -linoleic acid in response to marked changes in their dietary intake in men*, Journal of Lipid Research, vol. 46, No. 2, pp. 269-280, Dec. 1, 2004.
Jacquot et al, *Isotope sensitive Branching and Kinetic Isotope Effects in the Reaction of Deuterated Arachindonic Acids with Human 12- and 15-Lipoxygenases +*, Biochemistry, vol. 47, No. 27, pp. 7295-7303, Jun. 12, 2008.
Johnson et al, *Potential role of dietary n-3 fatty acids in the prevention of dementia and macular degeneration*, The American Journal of Clinical Nutrition, vol. 83, No. 6, pp. S1494-1498S, Jun. 2006.
Mazza et al, *Omega-3 fatty acids and antioxidants in neurological and psychiatric diseases: An overview*, Progress in Neuro-Psychopharmacology & Biological Psychiatry, Oxford, GB, vol. 31, No. 1, pp. 12-26, Dec. 22, 2006.
Shchepinov et al, *Isotopic reinforcement of essential polyunsaturated fatty acids diminishes nigrostriatal degeneration in a mouse model of Parkinson's disease*, Toxicology Letter, Elsevier Biomedical Press, Amsterdam, NL, vol. 207, No. 2, pp. 97-103, Aug. 10, 2011.
Supplementary European Search Report & Written Opinion dated Jun. 5, 2013 for EP Application No. 10827578.5.
Gueraud et al., Chemistry and biochemistry of lipid peroxidation products, Free Radical Research, Oct. 2010, vol. 44, No. 10, pp. 1098-1124.
Riediger et al., A Systemic Review of the Roles of n-3 Fatty Acids in Health and Disease, Journal of the American Dietetic Association, Apr. 2009, pp. 668-679.

\* cited by examiner

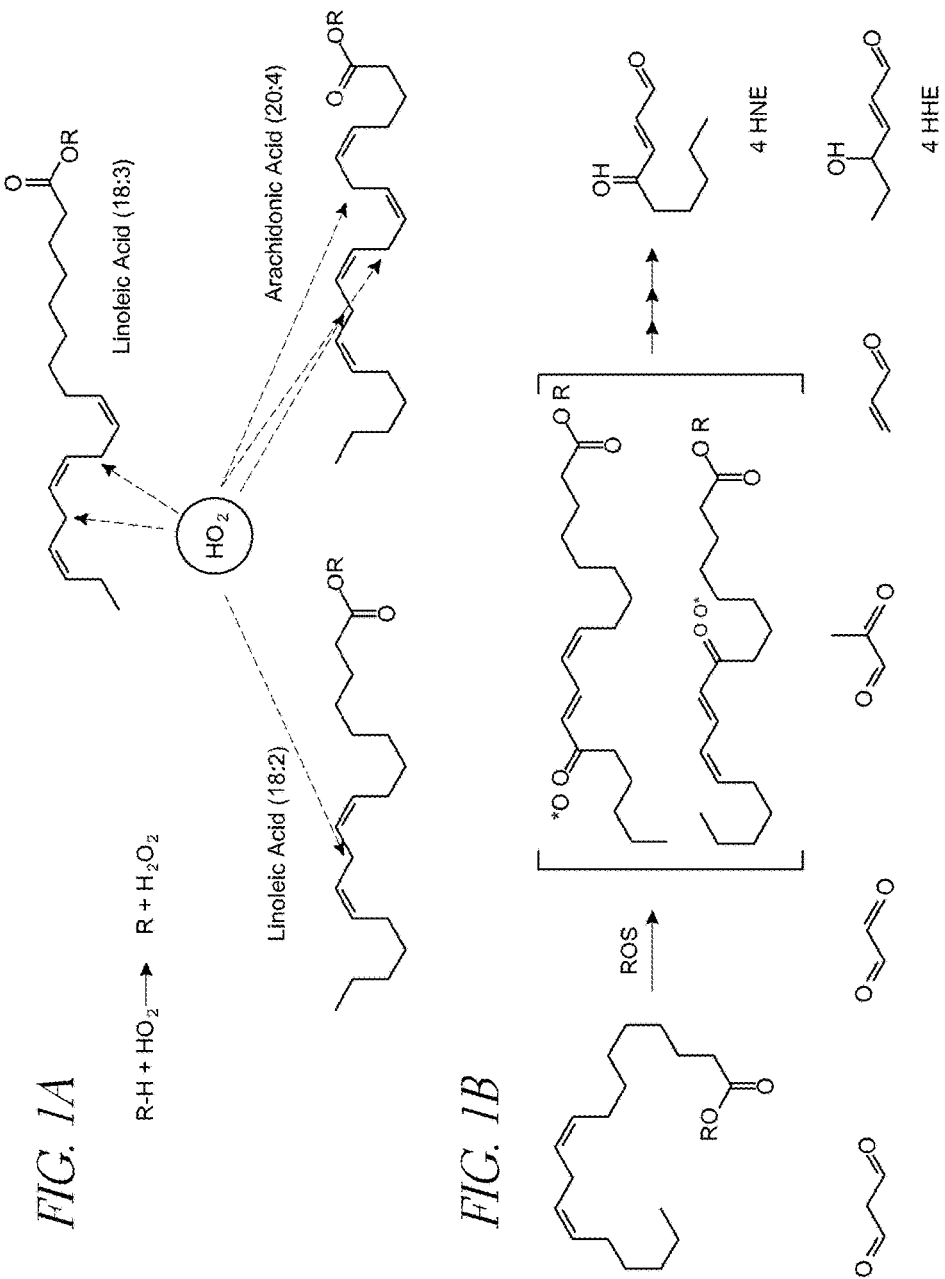

H-PUFA SAL
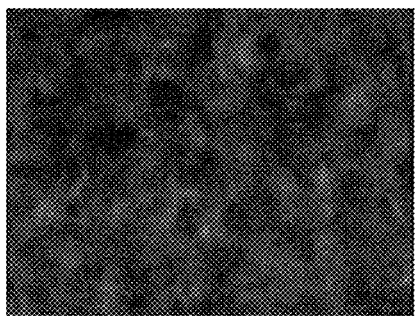
H-PUFA MPTP
D-PUFA SAL
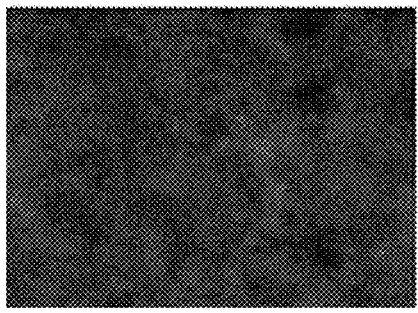
D-PUFA MPTP
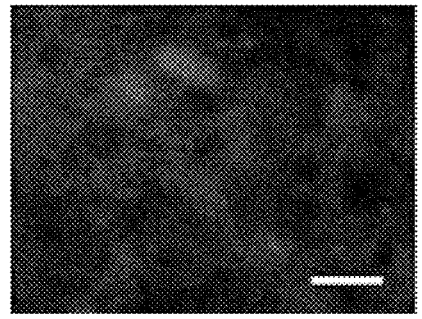
*FIG. 10*

ALLEVIATING OXIDATIVE STRESS DISORDERS WITH PUFA DERIVATIVES

CROSS-REFERENCE TO RELATED APPLICATIONS

This application claims priority to U.S. Provisional Application No. 61/256,815, which is incorporated herein by reference in its entirety.

BACKGROUND

Field

Isotopically modified polyunsaturated fatty acids (PUFAs) and other modified PUFAs are useful in methods of treating certain diseases.

Description of the Related Art

U.S. application Ser. No. 12/281,957 assigned to the same assignees as the present application, refers to a class of compounds that, when ingested, result in the formation of bodily constituents, for example, fats that are functionally equivalent to normal bodily constituents but which have a greater resistance to degradative/detrimental processes such as those mediated by reactive oxygen species (ROS), reactive nitrogen species (RNS) or radiation. This application, which is incorporated herein by reference, refers to an essential nutrient in which at least one exchangeable H atom is $^2$H and/or at least one C atom is $^{13}$C. This application also discloses 11,11 dideutero linoleic acid.

11,11 dideutero linoleic acid and 11,11,14,14 D4 linolenic acid and similar compounds wherein the C atom in the deuterated methylene group may be $^{13}$C is disclosed. Shchepinov, M, Reactive Oxygen Species, Isotope Effect, Essential Nutrients, and Enhanced Longevity, Rejuvenation Research, vol. 10, no. 1, (2007). This article is incorporated herein by reference.

Although oxidative stress may be associated with various diseases, it is unpredictable which antioxidants will be successful in treating various diseases. Thus, there is a need in the art for successful treatment for various diseases. Therefore, there is a need in the art for additional isotopically modified polyunsaturated fatty acids (PUFAs) and other modified PUFAs useful for treating various diseases.

Replacing certain positions of PUFAs may also prevent or slow the helpful metabolic processes in which PUFAs are involved, and thus it would be helpful to the art to determine modified PUFAs that will sufficiently maintain these metabolic processes while resisting detrimental oxidative processes.

It would also be helpful to the art to determine the minimum amount of heavy atoms substitution necessary to prevent detrimental oxidative processes to save costs on heavy atom substitution. These and other aspects are addressed herein.

SUMMARY

The present disclosure addresses these needs and the need for additional isotopically modified polyunsaturated fatty acids (PUFAs), mimetic or ester pro-drug thereof. Further, present disclosure addresses the need for new methods of treating and preventing specific diseases using modified PUFAs in subjects such as human subjects.

Some embodiments include a method of treating or preventing the progression of a neurodegenerative disease comprising selecting a subject that has a neurodegenerative disease or is susceptible to a neurodegenerative disease; administering an effective amount of isotopically modified polyunsaturated fatty acid, mimetic or ester pro-drug thereof to the subject; wherein upon administration, the isotopically modified polyunsaturated fatty acid, mimetic or ester pro-drug thereof is incorporated in brain and/or neuronal tissue of the subject. The patient who has a neurodegenerative disease may include a subject with a) Alzheimer's disease or is susceptible to Alzheimer's disease; b) has mild cognitive impairment or is susceptible to mild cognitive impairment; c) has Parkinson's disease or is susceptible to Parkinson's disease; d) has schizophrenia or is susceptible to schizophrenia; e) has a bipolar disorder or is susceptible to a bipolar disorder; f) has amyotrophic lateral sclerosis or is susceptible to amyotrophic lateral sclerosis, among other diseases.

Some embodiments include a method of treating or preventing the progression of an oxidative disease of the eye comprising selecting a subject that has an oxidative disease of the eye or is susceptible to an oxidative disease of the eye; administering an effective amount of at least one isotopically modified polyunsaturated fatty acid, mimetic or ester pro-drug thereof to the subject; wherein upon administration, the isotopically modified polyunsaturated fatty acid, mimetic or ester pro-drug thereof is incorporated in eye tissue of the subject. The subject with oxidative disease of the eye may include a subject having retinal disease or is susceptible to a retinal disease, having age related macular degeneration or is susceptible to age related macular degeneration, having diabetic retinopathy or is susceptible to diabetic retinopathy, or having retinitis pigmentosa or is susceptible to retinitis pigmentosa, among other diseases.

Additional embodiments include a method comprising selecting a subject in need of increased levels of high-density lipoprotein and/or decreased levels of low-density lipoprotein; administering an effective amount of isotopically modified polyunsaturated fatty acid, mimetic or ester pro-drug thereof to the subject; and wherein upon administration, the level of high-density lipoprotein is increased and/or the level of low-density lipoprotein is decreased. Subjects may include those with atherosclerotic vascular disease or susceptible to atherosclerotic vascular disease, among other diseases.

Further embodiments include a method of treating or preventing the progression of a mitochondrial deficiency or mitochondrial respiration deficiency disease, such as a Coenzyme Q10 deficiency, comprising selecting a subject that has a mitochondrial deficiency or mitochondrial respiration deficiency diseases such as a Coenzyme Q10 deficiency or is susceptible to mitochondrial deficiency or mitochondrial respiration deficiency disease comprising administering an effective amount of isotopically modified polyunsaturated fatty acid, mimetic or ester pro-drug thereof to the subject; wherein upon administration, the isotopically modified polyunsaturated fatty acid, mimetic or ester pro-drug thereof is incorporated in mitochondrial membrane of the subject. Subjects having other mitochondrial deficiency or mitochondrial respiration deficiency diseases include a) nervous system disease or is susceptible to a nervous system disease, b) dyskinesia or is susceptible to dyskinesia, c) ataxia or is susceptible to ataxia, d) musculoskeletal disease or is susceptible to a musculoskeletal disease, e) muscle weakness or is susceptible to muscle weakness, f) a neuromuscular disease or is susceptible to a neuromuscular disease, or g) a metabolic disease or is susceptible to a metabolic disease.

Methods also include a method of treating an inborn error of metabolism comprising selecting a subject that has an inborn error of metabolism, administering an effective amount of isotopically modified polyunsaturated fatty acid, mimetic or ester pro-drug thereof to the subject; wherein upon administration, the isotopically modified polyunsaturated fatty acid, mimetic or ester pro-drug thereof is incorporated in brain and/or neuronal tissue of the subject. The inborn error of metabolism may be Down's syndrome, for example.

In some embodiments, a method comprises administering to a subject a sufficient amount of an isotopically modified PUFA, wherein a cell or tissue of the subject maintains a sufficient concentration of isotopically modified PUFAs to maintain autooxidation of the PUFAs.

Compounds and compositions are also contemplated such as a polyunsaturated fatty acid composition comprising an isotopically modified polyunsaturated fatty acid, mimetic or ester pro-drug thereof comprising at least one $^{13}C$ or at least two deuterium atoms at a bis-allylic position, or a mimetic or mimetic ester thereof, wherein the composition is suitable for human consumption, wherein the isotopically modified polyunsaturated fatty acid or ester thereof or mimetic or mimetic ester thereof is capable of retaining its chemical identity when incorporated in a bodily constituent of the subject following ingestion or uptake by the subject, or is capable of conversion into higher homolog of the polyunsaturated fatty acid or mimetic thereof in the subject; wherein the amount of isotopes in the isotopically modified polyunsaturated fatty acid is above the naturally-occurring abundance level; and with the proviso wherein the isotopically modified polyunsaturated fatty acid is not 11,11,14,14, D4-linolenic acid or 11,11,D2-linoleic acid. The isotopically modified polyunsaturated fatty acid or mimetic thereof may be an isotopically modified polyunsaturated fatty acid selected from the group consisting of 11,11,14,14, D4-linoleic acid, 11,11,D2-linolenic acid, and 14,14,D2-linolenic acid. The isotopically modified polyunsaturated fatty acid, mimetic or ester pro-drug thereof may be an isotopically modified polyunsaturated fatty acid further comprising deuterium at a pro-bis-allylic position. The isotopically modified polyunsaturated fatty acid, mimetic or ester pro-drug thereof may be a mimetic selected from the group consisting of Octadeca-8,12-dienoic acid Octadeca-7,11,15-trienoic acid R = H, C$_3$H$_7$; R$^1$ = H; alkyl; n = 1-4; m = 1-12

X = S: 10-Hept-1-enylsulfanyl-dec-9-enoic acid
X = O: 10-Hept-1-enyloxy-dec-9-enoic acid X = S: 10-(2-But-1-enylsulfanyl-vinylsulfanyl)-dec-9-enoic acid
X = O: 10-(2-But-1-enyloxy-vinyloxy)-dec-9-enoic acid R = H, C$_3$H$_7$; R$^1$ = H; alkyl; X = O; S; n = 1-5; m = 1-12

11,11-Dimethyl-octadeca-9,12-dienoic acid 11,11,14,14-Tetramethyl-octadeca-9,12,15-trienoic acid R = H, C$_3$H$_7$; R$^1$ = H; alkyl; n = 1-5; m = 1-12

10-(1-Hept-1-enyl-cyclopropyl)-dec-9-enoic acid

10-{1-[2-(1-But-1-enyl-cyclopropyl)-vinyl]-cyclopropyl}-dec-9-enoic acid

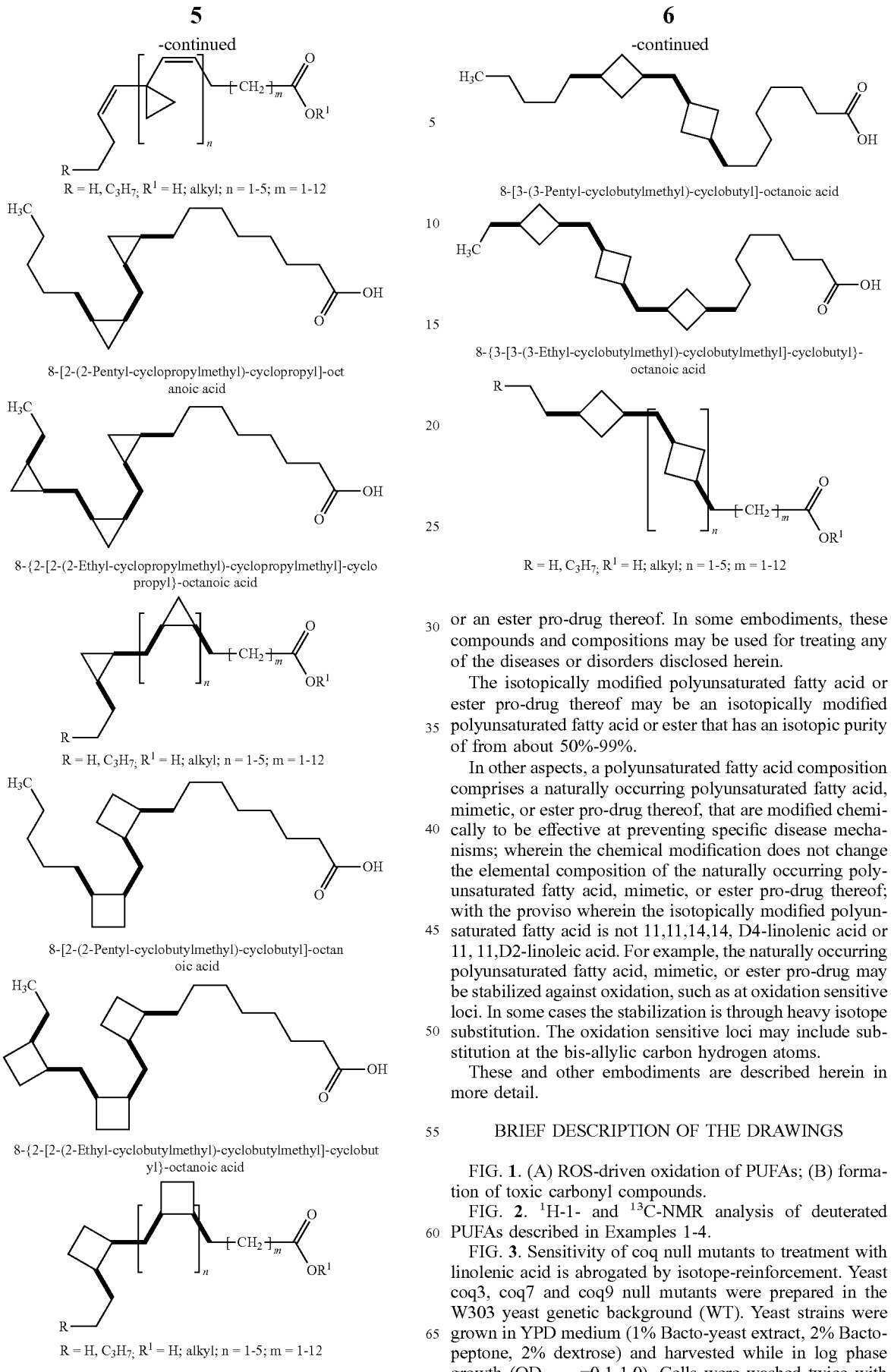

or an ester pro-drug thereof. In some embodiments, these compounds and compositions may be used for treating any of the diseases or disorders disclosed herein.

The isotopically modified polyunsaturated fatty acid or ester pro-drug thereof may be an isotopically modified polyunsaturated fatty acid or ester that has an isotopic purity of from about 50%-99%.

In other aspects, a polyunsaturated fatty acid composition comprises a naturally occurring polyunsaturated fatty acid, mimetic, or ester pro-drug thereof, that are modified chemically to be effective at preventing specific disease mechanisms; wherein the chemical modification does not change the elemental composition of the naturally occurring polyunsaturated fatty acid, mimetic, or ester pro-drug thereof; with the proviso wherein the isotopically modified polyunsaturated fatty acid is not 11,11,14,14, D4-linolenic acid or 11, 11,D2-linoleic acid. For example, the naturally occurring polyunsaturated fatty acid, mimetic, or ester pro-drug may be stabilized against oxidation, such as at oxidation sensitive loci. In some cases the stabilization is through heavy isotope substitution. The oxidation sensitive loci may include substitution at the bis-allylic carbon hydrogen atoms.

These and other embodiments are described herein in more detail.

BRIEF DESCRIPTION OF THE DRAWINGS

FIG. 1. (A) ROS-driven oxidation of PUFAs; (B) formation of toxic carbonyl compounds.

FIG. 10. D-PUFA partially attenuates MPTP-induced nigral a-syn accumulation in C57BL/6 mice. Mice, aged 8 weeks, were fed fat-free diet supplemented with either D-PUFAs or H-PUFAs for 6 days, exposed to 40 mg/kg MPTP, i.p., or saline, continued on D- or H-PUFA diet and sacrificed 6 days later. Immunoreactivity for a-syn was observed in sections from the substantia nigra of the cohorts. While neuropil staining was apparent in both saline-treated groups, robust cell body staining was noted in H-PUFA-fed, MPTP-treated mice. An apparent reduction in the intensity and number of a-syn-positive cell bodies was observed in the D-PUFA-fed, MPTP-treated cohort by comparison. Bar=25 µm.

DETAILED DESCRIPTION OF THE PREFERRED EMBODIMENT

Figure 2A:
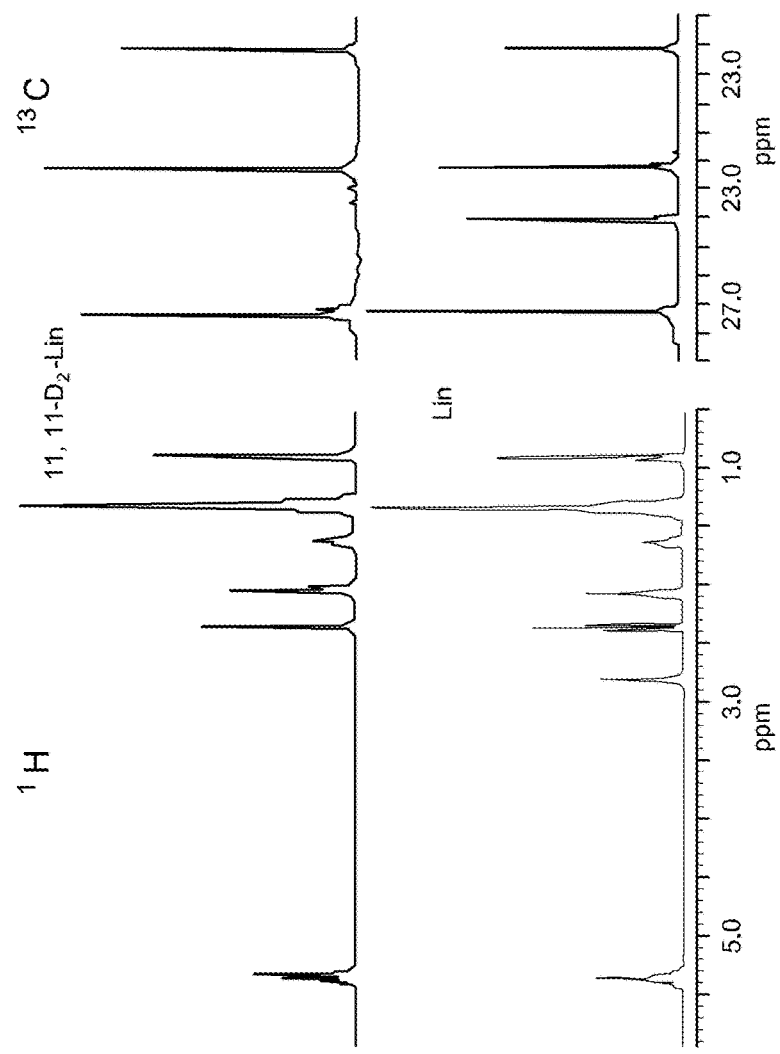
FIG. 2. $^1$H-1- and $^{13}$C-NMR analysis of deuterated PUFAs described in Examples 1-4.

As an introduction, lipid-forming fatty acids are well-known as one of the major components of living cells. As such, they participate in numerous metabolic pathways, and play an important role in a variety of pathologies. Essential Polyunsaturated Fatty Acids (PUFAs) are an important subclass of fatty acids. An essential nutrient is a food component that directly, or via conversion, serves an essential biological function and which is not produced endogenously or in large enough amounts to cover the requirements. For homeothermic animals, the two rigorously essential PUFAs are linoleic (cis,cis-9,12-Octadecadienoic acid; (9Z,12Z)-9,12-Octadecadienoic acid; LA; 18:2; n-6) and alpha-linolenic (cis,cis,cis-9,12,15-Octadecatrienoic acid; (9Z,12Z,15Z)-9,12,15-Octadecatrienoic acid; ALA; 18:3; n-3) acids, formerly known as vitamin F (Cunnane S C. Progress in Lipid Research 2003; 42:544-568). LA, by further enzymatic desaturation and elongation, is converted into higher n-6 PUFAs such as arachidonic (AA; 20:4; n-6) acid; whereas ALA gives rise to a higher n-3 series, including, but not limited to, eicosapentaenoic acid (EPA; 20:5; n-3) and docosahexaenoic (DHA; 22:6; n-3) acid (Goyens P L. et al. *Am. J. Clin. Nutr.* 2006; 84:44-53). Because of the essential nature of PUFAs or PUFA precursors, there are many instances of their deficiency. These are often linked to medical conditions. Many PUFA supplements are available over-the-counter, with proven efficiency against certain ailments (For example, U.S. Pat. No. 7,271,315, U.S. Pat. No. 7,381,558).

Brain tissue is particularly rich in PUFAs, which constitute 35% of the phospholipids in the neuronal membranes of the brain (Hamilton J A. et al. *J. Mol. Neurosci.* 2007; 33:2-11). Three particularly important fatty acids, which are abundant in neuronal membranes, are: LA, which makes up cardiolipin; DHA, deficiencies of which can impede brain development and compromise optimal brain function; and AA, which yields essential, but potentially toxic, metabolic products.

PUFAs endow membranes, in particular mitochondrial membranes, with appropriate fluidity necessary for optimal oxidative phosphorylation performance. PUFAs also play an important role in initiation and propagation of the oxidative stress. PUFAs react with ROS through a chain reaction that amplifies an original event (Sun M, Salomon R G, *J. Am. Chem. Soc.* 2004; 126:5699-5708). Of particular importance is a mitochondrial membrane-specific PUFA-rich phospholipid cardiolipin, vital for electron transport Complex I activity (Paradies G, et al. *Gene* 2002; 86:135-141).

Non-enzymatic formation of high levels of lipid hydroperoxides is known to result in several detrimental changes. It negatively affects the fluidity and permeability of the membranes; leads to oxidation of membrane proteins; and these hydroperoxides can be converted into a large number of highly reactive carbonyl compounds. The latter include reactive species such as acrolein, malonic dialdehyde, glyoxal, methylglyoxal, etc (Negre-Salvayre A, et al. *Brit. J. Pharmacol.* 2008; 153:6-20). But the most prominent products of PUFAs oxidation are alpha, beta-unsaturated aldehydes 4-hydroxynon-2-enal (4-HNE; formed from n-6 PUFAs like LA or AA), 4-hydroxyhex-2-enal (4-HHE; formed from n-3 PUFAs like ALA or DHA), and corresponding ketoaldehydes (Esterfbauer H, et al. *Free Rad. Biol. Med.* 1991; 11:81-128; Long E K, Picklo M J. *Free Rad. Biol. Med.* 2010; 49:1-8). These reactive carbonyls cross-link (bio)molecules through Michael addition or Schiff base formation pathways, and have been implicated in a large number of pathological processes, age-related and oxidative stress-related conditions and aging. Importantly, in some cases, PUFAs appear to oxidize at specific sites because methylene groups of 1,4-diene systems (the bis-allylic position) are substantially less stable to ROS, and to enzymes such as cyclogenases and lipoxygenases than allylic methylenes.

There are many diseases that are oxidative stress-related, including, but not limited to, neurological diseases, diabetes, diseases associated with elevated concentration of low density lipoprotein (LDL), and AMD. While the exact aetiology of many such diseases requires further clarification, PUFAs oxidation, and consequent cross-linking or derivatisation with reactive carbonyls, often plays a prominent role. The role of oxidative stress in Age-related Macular Degeneration (AMD) is known to be quite prominent (Beatty S, et al. *Survey Ophtalm.* 2000; 45:115-134; (de Jong Paulus T V M Age-related macular degeneration. The New England journal of medicine 2006; 355(14): 1474-85.); Wu J, Seregard S, et al. *Survey Ophtalm.* 2006; 51:461-481). Almost all major neurological diseases are known to be linked to oxidative stress. For instance, oxidized membrane components accelerate beta- and alpha-synuclein aggregation, associated with Alzheimer's disease (AD) and Parkinson's disease (PD) and synucleinopathies, by covalent and noncovalent mechanisms, respectively. Reactive products of PUFA peroxidation can trigger protein misfolding in sporadic amyloid diseases, which are the clinically most important neurological brain diseases (Bieschke J. et al, *Acc. Chem. Res.* 2006; 39:611-619).

Some examples of disorders involving PUFA peroxidation and reactive compounds formed from peroxidized PUFAs include, but are not limited to:

Age-Related Macular Degeneration (AMD), Retinitis Pigmentosa (RP) and Diabetic Retinopathy (DR)

Increased oxygen levels, exposure to light and high PUFA content lead to increased PUFA peroxidation in the eye tissues. Oxidative stress plays a major role in the pathogenesis of AMD (Beatty S, et al. *Survey Ophtalm.* 2000; 45:115-134). Increased levels of PUFA peroxidation products such as HNE and HHE have been reported in retina (Long E K, et al. *Free Rad. Biol. Med.* 2010; 49:1-8). PUFA peroxidation products play a major role in formation of retinal pigment epithelial (RPE) lipofuscin, which itself can generate ROS upon irradiation with visible light, and plays a major role in etiology of AMD (Katz M L, *Arch. Gerontol. Geriatr.* 2002; 34:359-370). PUFA peroxidation products, including MDA, play such a prominent role in lens pathologies including formation of cataracts, that the PUFA peroxidation was proclaimed to be an initiating step in the human cataract pathogenesis (Borchman D. et al, *J. Lipid Res.* 2010; 51:2473-2488). Equally important is the role of PUFA peroxidation products in pathophysiology of diseases of human cornea, including pterygium and keratoconus (Shoham A, et al. *Free Rad. Biol. Med.* 2008; 45:1047-1055). Diabetic retinopathy is also associated with oxidative stress and PUFA peroxidation (Baynes J W, Thorpe S R. *Diabetes* 1999; 48:1-9).

In some aspects, identification of a subject who has or is susceptible to AMD, RP or DR may be determined by diagnostic tests known in the art such as fluorescein angiography or by identifying abnormalities in vascular processes. In addition, Optial Coherence Tomography diagnostics may be used to identify such subjects.

Alzheimer's Disease (AD) and Mild Cognitive Impairment (MCI)

See Cooper J L. *Drugs & Aging* 2003; 20:399-418. Amyloid plaques and neurofibrillary tangles are the neuropathological hallmarks of AD, although whether they are the cause or the product of the disease is still debatable. Oxidative stress, and a related inflammation, is implicated in the AD process. The direct evidence supporting increased oxidative stress in AD is: (1) increased ROS-stimulating Fe, Al, and Hg in AD brain; (2) increased PUFA peroxidation and decreased PUFAs in the AD brain, and increased 4-HNE in AD ventricular fluid; (3) increased protein and DNA oxidation in the AD brain; (4) diminished energy metabolism and decreased cytochrome c oxidase in the brain in AD; (5) advanced glycation end products (AGE), MDA, carbonyls, peroxynitrite, heme oxygenase-1 and SOD-1 in neurofibrillary tangles and AGE, heme oxygenase-1, SOD-1 in senile plaques; and (6) studies showing that amyloid beta peptide is capable of generating ROS (Markesbery W R. *Free Rad. Biol. Med.* 1997; 23:134-147).

The abnormalities of lipid metabolism play a prominent role in AD. All proteins involved in Amyloid precursor protein processing and Ab peptide production are integral membrane proteins. Moreover, the Ab producing c-secretase cleavage takes place in the middle of the membrane, so the lipid environment of the cleavage enzymes influences Ab production and AD pathogenesis (Hartmann T. et al, *J. Neurochem.* 2007; 103:159-170). Lipid peroxidation is marked by high levels of malondialdehyde, isoprostanes, and high level of protein modification by HNE and acrolein (Sayre L M, et al. *Chem. Res. Toxicol.* 2008; 21:172-188; Butterfield D A, et al. *Biochim. Biophys. Acta* 2010; 1801: 924-929). Dietary PUFAs are the principal risk factor for the development of late-onset sporadic AD. The degree of saturation of PUFAs and the position of the first double bond are the most critical factors determining the risk of AD, with unsaturated fats and n-3 double bonds conferring protection and an overabundance of saturated fats or n-6 double bonds increasing the risk. DHA and AA are particularly relevant to AD (Luzon-Toro B, et al. *Neurol. Psychiatr. Brain Res.* 2004; 11:149-160). DHA is the major component of excitable membranes, promotes maturation in infants and is a potent neuroprotective agent in the adult brain, with a potential role in the prevention of AD. AA is an important provider of eicosanoids, acting as a second messenger in many neurotransmitter systems. The interaction of dietary PUFAs and apolipoprotein E isoforms may determine the risk and rate of sustained autoperoxidation within cellular membranes and the efficacy of membrane repair.

It has been reported that lipid peroxidation is present in the brain of MCI patients. Several studies established oxidative damage as an early event in the pathogenesis of AD, that can serve as a therapeutic target to slow the progression or perhaps the onset of the disease. (Markesbery W R. *Arch. Neurol.* 2007; 64:954-956). MCI can also be characterized by elevated levels of conjugates formed by lipid peroxidation products such as MDA, HNE, acrolein and isoprostanes (Butterfield D A, et al. *Biochim. Biophys. Acta* 2010; 1801: 924-929).

Identifying subjects with Alzheimer's disease or susceptible to Alzheimer's disease are known in the art. For instance, subjects may be identified using criteria set forth by the National Institute of Neurological and Communicative Disorders and Stroke (NINCDS)-Alzheimer's Disease an Related Disorders Association (ADRDA). The criteria are related to memory, language, perceptual skills, attention, constructive abilities, orientation, problem solving and functional abilities. Similar diagnostic tests may be used to identify MCI patients.

Amyotrophic Lateral Sclerosis (ALS)

ALS is a late-onset progressive neurodegenerative disease affecting motor neurons (loss of upper and lower motor neurons), culminating in muscle wasting and death from respiratory failure (Boillee S. et al, *Neuron* 2006; 52:39-59). The etiology of most ALS cases remains unknown; however, it is recognized that ALS is strongly associated with oxidative stress. Familial ALS (fALS) is caused by oxidation of mutated SOD (superoxide dismutase) (Kabashi E. et al, *Ann. Neurol.* 2007; 62:553-559). There are more than 100 mutations in SOD that are associated with the fALS (Barnham K J et al, *Nature Rev. Drug Discov.* 2004; 3:205-214). The first step is the 'monomerisation' of SOD, which then leads to the aggregation of SOD monomers, which then form aberrant S—S bonds between themselves (Kabashi E. et al, *Ann. Neurol.* 2007; 62:553-559), yielding conglomerates which are toxic (either because they mis-fold and clog things up, or both (Barnham K J et al, *Nature Rev. Drug Discov.* 2004; 3:205-214).

fALS-associated SOD1 mutations were shown to be linked with the loss of redox sensor function in NADPH oxidase-dependent ROS production, leading to microglial neurotoxic inflammatory responses, mediated by an uncontrolled ROS generation (Liu Y, Hao W L, et al. *J. Biol. Chem.* 2009; 284:3691-3699). Sporadic ALS (sALS) is more common (90% cases).

The aetiology of ALS cases remains unknown, but it is recognized that ALS is associated with oxidative stress and inflammation. Protein oxidation is increased 85% in sALS patients in one study (Coyle J T. et al, *Science* 1993; 262:689-695). And both increased lipid peroxidation and HNE formation were reported for ALS cases, both familial and sporadic (Simpson E P et al, *Neurology* 2004; 62:1758-1765), in the central nervous system (CNS) tissue, spinal fluid, and serum. The source of the oxidative stress in ALS is not clear but may derive from several processes including excitotoxicity, mitochondrial dysfunction, iron accumulation or immune activation (Simpson E P et al, *Neurology* 2004; 62:1758-1765). There is evidence that mitochondria play an important role in fALS and sALS, being both a trigger and a target for oxidative stress in ALS (Bacman S R et al, *Molec. Neurobiol.* 2006; 33:113-131). Inhibition of COX-2 has been reported to reduce spinal neurodegeneration and prolong the survival of ALS transgenic mice (Minghetti L. *J Neuropathol Exp Neurol* 2004; 63:901-910), highlighting the role for PUFA oxidation products in the etiology of ALS. There is also evidence of increased HHE-protein conjugation in ALS patients (Long E K, Picklo M J. *Free Rad. Biol. Med.* 2010; 49:1-8). Despite of oxidative stress being associated with ALS, trials of antioxidant therapies so far failed (Barber S C et al. *Biochim. Biophys. Acta* 2006; 1762:1051-1067).

Identifying a subject having or at risk for developing ALS may be determined using diagnostic methods known in the art. For example, one or a combination of tests may be used such as upper and lower motor neuron signs in a single limb; electromyography (EMG); nerve conduction velocity (NCV) measurement to rule out peripheral neuropathy and myopathy; magnetic resonance imaging (MRI); and/or blood and urine testing to eliminate a possibility of other diseases.

Other CNS diseases that may be treated by the compounds disclosed herein are also contemplated and include degenerative neurological and neuromuscular diseases and disorders such as Jacobson Syndrome, Spinal Muscular Atrophy, and Multiple System Atrophy, among others.

Atherosclerotic Vascular Disease (ASVD)

This condition, which is a result of a build-up of fatty materials affecting blood vessels, results in many pathologies including myocardial infarction and stroke. PUFA peroxidation products play a very important role in formation and accumulation of low density lipopolyprotein (LDL, 'bad fat') (Esterbauer H, et al. *Free Rad. Biol. Med.* 1991; 11:81-128; Requena J R et al, *Biochem. J.* 1997; 322:317-325). Numerous diagnostic tests are available to identify subjects having atherosclerotic vascular disease.

In some embodiments, the ratio of HDL to LDL is significantly increased upon administration of modified PUFAs described herein. For example, in Table 3 below, an increase of approximately 86% of the HDL:LDL ratio upon administration of D-PUFA was found in comparison to the HDL:LDL ratio upon administration the H-PUFA. This percentage is based upon the calculation wherein the LDL level equals the total cholesterol minus the HDL level and minus 20% of the triglyceride level. In some aspects, the HDL-LDL ratio increases upon administration (such as over the course of an administration protocol) of the modified PUFA at least about 5%, such as at least about 10%, 20%, 30%, 40%, 50%, 60%, 70%, 80%, 90%, 100%, 110%, 120%, 130%, 140%, or more in comparison to the HDL:LDL ratio before administration.

Mitochondrial Diseases Such as Coenzyme Q10 Deficiency (Q10−)

Mitochondrial deficiency or mitochondrial respiration deficiency diseases include diseases and disorders caused by oxidation of mitochondrial membrane elements, such as mitochondrial respiration deficiency, which occurs in the membrane. Membrane functionality is important to overall mitochondrial function.

Coenzyme Q deficiency is associated with many diseases, including nervous system diseases (dyskinesias, ataxia); musculoskeletal diseases (muscle weakness, neuromuscular diseases); metabolic diseases etc. Q10 plays an important role in controlling the oxidative stress. Q10− has been shown to be linked to increased PUFA toxicity, through PUFA peroxidation and toxicity of the formed products (Do T Q et al, *PNAS USA* 1996; 93:7534-7539). Numerous diagnostic tests are known in the art to identify subjects having a Coenzyme Q10 deficiency.

Down's Syndrome (DS)

DS (trisomy of chromosome 21) is associated with premature aging and mental retardation similar to Alzheimer's disease. The incidence of autoimmune diseases and cataracts is also elevated, pointing to increased oxidative stress in individuals with DS (Jovanovic S V, et al. *Free Rad. Biol. Med.* 1998; 25:1044-1048). Chromosome 21 codes for Cu/Zn SOD and amyloid beta-peptide, so the DS is characterised by the overflow of these gene products and metabolites, notably an increased ratio of SOD to catalase, accompanied by excessive $H_2O_2$ (Sinet P M. *Ann. NY Acad. Sci.* 1982; 396:83-94). In individuals with DS, the markers of protein and lipid oxidation (MDA, HNE, etc), and advanced glycation and lipoxidation end-products, are significantly increased (Busciglio J, Yankner B A. *Nature* 1995; 378:776-779; Odetti P, et al. *Biochem. Biophys. Res. Comm.* 1998; 243:849-851). The importance of oxidative stress in DS led to widespread attempts to reduce the side-effect of oxidation by employing antioxidants; but recent randomised trials found no evidence of efficiency of antioxidant supplements (Ellis J M, et al. *Brit. Med. J.* 2008; 336:594-597). Subjects with Down Syndrome may be identified by standard chromosomal testing.

Parkinson's Disease (PD)

PD is associated with oxidative stress caused by ROS, which contributes to a cascade leading to dopamine cell degeneration in PD. However, oxidative stress is intimately linked to other components of disease and degenerative processes, such as mitochondrial dysfunction, excitotoxicity, nitric oxide toxicity and inflammation. Formation of intracellular toxic lipid peroxides has been directly linked to damage in nigral neurons through activation of toxic cellular cascades. Oxidative damage associated with PD is initiated at the PUFAs level, and then passed on to proteins and nuclear DNA and mtDNA (for example, in synuclein processing/Lewy body formation), and toxic carbonyl products of oxidative damage, such as HNE and MDA, can further react with proteins to impair cell viability. Nitric oxide is known to react with superoxide to produce peroxynitrite and ultimately hydroxyl radical. Altered degradation of proteins has been implicated as key to dopaminergic cell death in PD. Oxidative stress can impair these processes directly, and products of oxidative damage, such as HNE, can damage the 26S proteasome. HNE has been directly implicated in the pathogenesis of PD (Selley M L. *Free Rad. Biol. Med.* 1998; 25:169-174; Zimniak P, *Ageing Res. Rev.* 2008; 7:281-300). Furthermore, impairment of proteasomal function leads to free radical generation and oxidative stress (Jenner P. *Annals Neurol.* 2003; 53: S26-S36). An additional source of ROS relevant to PD etiology is dopamine (DA) turnover in dopaminergic neurons (Hastings T G, J. *Bioenerg. Biomembr.* 2009; 41:469-72). Oxidative damage to nucleic acids, mediated through PUFA peroxidation products, also contributes to etiology of PD (Martin L J, *J. Neuropathol. Exp. Neurol.* 2008; 67:377-87; Nakabeppu Y. et al., *J. Neurosci. Res,* 2007; 85:919-34). Whether or not oxidative stress is the cause or the consequence of PD, reducing it is likely to affect the progression of the disease.

Identifying a subject that has or is susceptible to Parkinson's disease may be determined by various tests known in the art. For example, a combination of tests and diagnosis may be based on medical history and neurological examination, including, for example, positive response to levodopa. In addition, the identification of a subject may be determined according to diagnostic criteria of Parkinson's Disease Society Brain Bank and the National Institute of Neurological Disorders and Stroke, such as bradykinesia and rigidity and/or rest tremor and/or postural instability.

Schizophrenia and Bipolar Disorder (BD)

PUFAs are known to influence neurodevelopment and some psychiatric disorders, such as schizophrenia. DHA, eicosapentaenoic acid (EPA) and AA are of particular importance in this regard. In schizophrenia, there is a positive correlation between EPA supplementation and the improvement of some symptoms, (Luzon-Toro B, et al. *Neurol. Psychiatr. Brain Res.* 2004; 11:149-160). There is a significant increase in oxidative stress and HNE levels in both Schizophrenia and BD (Wang J F, et al. *Bipolar Disorders* 2009; 11:523-529). Synaptic dysfunction is known to be an early pathogenic event in neuropathologies such as AD, ALS, PD, etc. (LoPachin R M et al *Neurotoxicol.* 2008; 29:871-882). Although the molecular mechanism of this synaptotoxicity is not known, published evidence suggests that these diseases are characterized by a common pathophysiological cascade involving oxidative stress, PUFA peroxidation (FIG. 1) and the subsequent liberation of $\alpha,\beta$-unsaturated carbonyl derivatives such as acrolein and 4-HNE.

Numerous diagnostic tests are known in the art to identify subjects having schizophrenia or bipolar disorder.

The latest research suggests that the strongest detrimental effect on the aetiology of oxidative stress-related diseases, including neurological disorders, is exercised not by oxidative stress or ROS, but specifically by electrophilic toxicity of reactive carbonyl compounds (Zimniak P, *Ageing Res. Rev.* 2008; 7:281-300). These carbonyl compounds can cause nerve terminal damage by forming adducts with presynaptic proteins. Therefore, the endogenous generation of acrolein and HNE in oxidatively stressed neurons of certain brain regions is mechanistically related to the synaptotoxicity associated with neurodegenerative conditions.

In addition, acrolein and HNE are members of a large class of structurally related chemicals known as the type-2 alkenes. Chemicals in this class (e.g., acrylamide, methylvinyl ketone, and methyl acrylate) are pervasive pollutants in human environments and new research has shown that these $\alpha,\beta$-unsaturated carbonyl derivatives are also toxic to nerve terminals. Regional synaptotoxicity, which develops during the early stages of many neurodegenerative diseases, is mediated by endogenous generation of reactive carbonyl compounds from oxidised PUFAs. Moreover, the onset and progression of this neuropathogenic process is accelerated by environmental exposure to other type-2 alkenes.

Increased concentrations of 4-HNE (5-10 mM) and other reactive carbonyls are involved in the pathogenesis of a number of degenerative diseases, and thus are widely accepted as inducers and mediators of oxidative stress (Uchida K. Prog. Lipid Res. 2003; 42:318-343). However, a normal, physiological (0.1-0.3 mM) concentration of cellular 4-HNE is required to modulate a wide variety of cellular processes and to activate numerous signaling pathways (Chen Z.-H., et al. IUBMB Life 2006; 58:372-373; Niki E. Free Rad. Biol. Med. 2009; 47:469-484). It is therefore desirable to decrease the concentration, but not to completely remove, reactive carbonyls from cells.

Enzymatic oxidation of PUFAs gives rise to eicosanoids and in particular to prostanoids, which comprise several important classes of biological mediators. Some of these mediators, in particular those formed from omega-6 PUFAs (prostaglandins and thromboxanes), have a strong pro-inflammatory effect and may initiate blood-clotting. Existing drugs such as aspirin have undesirable side-effects, so development of novel approaches to downregulate the enzymatic oxidation of PUFAs, and therefore their formation could be desirable.

The importance of oxidation of essential PUFAs in development and progression of many neurological and other disorders served to encourage the development of interventions designed to reduce the oxidative stress, and the associated damages inflicted by reactive carbonyls. Such approaches have focused on neutralizing the oxidative species (antioxidant supplements). The success of such interventions has been limited. Some drawbacks of such an approach include (but are not limited to) the following points, relevant to both small molecule and enzymatic antioxidants: (a) the near-saturating amount of antioxidants already present in living cells means that any further increase, even if substantial, in the amount of antioxidants would have only incremental, if any, effect on the residual ROS levels (Zimniak P, *Ageing Res. Rev.* 2008; 7:281-300); (b) ROS play an important role in cell signalling, the interference with which may have a detrimental effect (Packer L, Cadenas E. *Free Rad. Res.* 2007; 41:951-952); (c) in specific physiological contexts/at specific sites, ROS have protective functions which can be attenuated by antioxidants (Salganik R I. *J. Am. Coll. Nutr.* 2001; 20:464 S-472S); (d) oxidised forms of antioxidants can themselves be harmful (Zimniak P, *Ageing Res. Rev.* 2008; 7:281-300); (e) moderate levels of ROS contribute to hormetic (adaptive) upregulation of protective mechanisms (Calabrese E J, et al. *Toxicol. Appl. Pharmacol.* 2007; 222:122-128); (f) reactive carbonyl compounds such as HNE and HHE are not of a free radical nature, and therefore cannot be neutralised by antioxidants. However, they are still capable of significantly altering cellular redox status by depleting cellular sulfhydryl compounds such as glutathione (GSH).

The rate of some reactions is affected by the nature of the isotopes of the atoms which the bond links. In general, bonds terminating in a heavy isotope will be less liable to cleavage than a bond terminating in a lighter isotope. Of particular note is that bonds between hydrogen atoms and other atoms are less liable to breakage if the hydrogen is $^2$H rather than $^1$H. A similar effect is seen when comparing the rate of cleavage of a bond between a carbon atom and another atom, where bonds with $^{13}$C are less liable to cleavage than bonds with $^{12}$C. This is known as the Isotope Effect, and is well described. Many isotopes are known to show this effect, as is described in *Isotope effects in chemical reactions*. (Collins C J, Bowman N S (eds) 1970 *Isotope effects in chemical reactions*).

Some aspects of this invention arise from: (1) an understanding that while essential PUFAs are vital for proper functioning of lipid membranes, and in particular of the mitochondrial membranes, their inherent drawback, i.e., the propensity to be oxidized by ROS with detrimental outcome, is implicated in many neurological diseases; (2) antioxidants cannot cancel the negative effects of PUFA peroxidation due to stochastic nature of the process and the stability of PUFA peroxidation products (reactive carbonyls) to antioxidant treatment, and (3) the ROS-driven damage of oxidation-prone sites within PUFAs may be overcome by using an approach that makes them less amenable to such oxidations, without compromising any of their beneficial physical properties. Some aspects of this invention describe the use of the isotope effect to achieve this, only at sites in essential PUFAs and PUFA precursors that matter most for oxidation, while other aspects contemplate other sites in addition to those that matter most for oxidation.

It will be appreciated by those skilful in the art that the same effect can be achieved by protecting oxidation-prone positions within PUFAs using other chemical approaches. Certain PUFA mimetics, while possessing structural similarity with natural PUFAs, will nevertheless be stable to ROS-driven and enzymatic oxidation due to structural reinforcement.

Thus, in some embodiments, an isotopically modified polyunsaturated fatty acid or a mimetic refers to a compound having structural similarity to a naturally occurring PUFA that is stabilized chemically or by reinforcement with one or more isotopes, for example $^{13}$C and/or deuterium. Generally, if deuterium is used for reinforcement, both hydrogens on a methylene group may be reinforced.

Some aspects of this invention provide compounds that are analogues of essential PUFAs with either one, several, or all bis-allylic positions substituted with heavy isotopes. In some embodiments, the $CH_2$ groups, which will become the bis-allylic position in a PUFA upon enzymatic conversion, are substituted with heavy isotopes, useful for the prevention or treatment of neurological disorders in which PUFA oxidation is a factor.

The bis-allylic position generally refers to the position of the polyunsaturated fatty acid or mimetic thereof that corresponds to the methylene groups of 1,4-diene systems. The pro-bis-allylic position refers to the methylene group that becomes the bis-allylic position upon enzymatic desaturation.

In some embodiments, the chemical identity of PUFAs, i.e., the chemical structure without regard to the isotope substitutions or substitutions that mimic isotope substitutions, remains the same upon ingestion. For instance, the chemical identity of essential PUFAs, that is, PUFAs that mammals such as humans do not generally synthesize, may remain identical upon ingestion. In some cases, however, PUFAs may be further extended/desaturated in mammals, thus changing their chemical identity upon ingestion. Similarly with mimetics, the chemical identity may remain unchanged or may be subject to similar extension/desaturation. In some embodiments, PUFAs that are extended, and optionally desaturated, upon ingestion and further metabolism may be referred to as higher homologs.

In some embodiments, naturally-occurring abundance level refers to the level of isotopes, for example $^{13}$C and/or deuterium that may be incorporated into PUFAs that would be relative to the natural abundance of the isotope in nature. For example, $^{13}$C has a natural abundance of roughly 1% $^{13}$C atoms in total carbon atoms. Thus, the relative percentage of carbon having greater than the natural abundance of $^{13}$C in PUFAs may have greater than the natural abundance level of roughly 1% of its total carbon atoms reinforced with $^{13}$C, such as 2%, but preferably greater than 5%, 10%, 15%, 20%, 25%, 30%, 35%, 40%, 45%, 50%, 65%, 60%, 65%, 70%, 75%, 80%, 85%, 90%, 95%, or 100% of $^{13}$C with respect to one or more carbon atoms in each PUFA molecule.

Regarding hydrogen, in some embodiments, deuterium has a natural abundance of roughly 0.0156% of all naturally occurring hydrogen in the oceans on earth. Thus, a PUFA having greater that the natural abundance of deuterium may have greater than this level or greater than the natural abundance level of roughly 0.0156% of its hydrogen atoms reinforced with deuterium, such as 0.02%, but preferably greater than 5%, 10%, 15%, 20%, 25%, 30%, 35%, 40%, 45%, 50%, 65%, 60%, 65%, 70%, 75%, 80%, 85%, 90%, 95%, or 100% of deuterium with respect to one or more hydrogen atoms in each PUFA molecule.

In some aspects, a composition of PUFAs contains both isotopically modified PUFAs and isotopically unmodified PUFAs. The isotopic purity is a comparison between a) the relative number of molecules of isotopically modified PUFAs, and b) the total molecules of both isotopically modified PUFAs and PUFAs with no heavy atoms. In some embodiments, the isotopic purity refers to PUFAs that are otherwise the same except for the heavy atoms.

In some embodiments, isotopic purity refers to the percentage of molecules of an isotopically modified PUFAs in the composition relative to the total number of molecules of the isotopically modified PUFAs plus PUFAs with no heavy atoms. For example, the isotopic purity may be about 5%, 10%, 15%, 20%, 25%, 30%, 35%, 40%, 45%, 50%, 65%, 60%, 65%, 70%, 75%, 80%, 85%, 90%, 95%, or 100% of the molecules of isotopically modified PUFAs relative to the total number of molecules of both the isotopically modified PUFAs plus PUFAs with no heavy atoms. In some embodiments, isotopic purity of the PUFAs may be from about 50%-99% of the total number of molecules of the PUFAs in the composition. Two molecules of an isotopically modified PUFA out of a total of 100 total molecules of isotopically modified PUFAs plus PUFAs with no heavy atoms, will have 2% isotopic purity, regardless of the number of heavy atoms the two isotopically modified molecules contain.

In some aspects, an isotopically modified PUFA molecule may contain two deuterium atoms, such as when the two hydrogens in a methylene group are both replaced by deuterium, and thus may be referred to as a "D2" PUFA. Similarly, an isotopically modified PUFA molecule may contain four deuterium atoms and may be referred to as a "D4" PUFA.

The number of heavy atoms in a molecule, or the isotopic load, may vary. For example, a molecule with a relatively low isotopic load may contain 2 or 4 deuterium atoms. In a molecule with a very high load, each hydrogen may be replaced with a deuterium. Thus, the isotopic load refers to the percentage of heavy atoms in each PUFA molecule. For example, the isotopic load may be about 5%, 10%, 15%, 20%, 25%, 30%, 35%, 40%, 45%, 50%, 65%, 60%, 65%, 70%, 75%, 80%, 85%, 90%, 95%, or 100% of the number of the same type of atoms in comparison to a PUFA with no heavy atoms of the same type (e.g. hydrogen would be the "same type" as deuterium). Unintended side effects are expected to be reduced where there is high isotopic purity in a PUFA composition but low isotopic load in a given molecule. For example, the metabolic pathways will be less affected by using in a PUFA composition with high isotopic purity but low isotopic load.

In some aspects, isotopically modified PUFAs impart an amount of heavy atoms in a particular tissue. Thus, in some aspects, the amount of heavy molecules will be a particular percentage of the same type of molecules in a tissue. For example, the number of heavy molecules may be about 1%-100% of the total amount of the same type of molecules. In some aspects, 10-50% the molecules are substituted with the same type of heavy molecules.

In some embodiments, a compound with the same chemical bonding structure as an essential PUFA but with a different isotopic composition at particular positions will have significantly and usefully different chemical properties from the unsubstituted compound. The particular positions with respect to oxidation, such as enzymatic oxidation or oxidation by ROS, comprise bis-allylic positions of essential polyunsaturated fatty acids and their derivatives, as shown in FIG. 1. The essential PUFAs isotope reinforced at bis-allylic positions shown below will be more stable to the oxidation. Accordingly, some aspects of the invention provide for particular methods of using compounds of Formula (1), whereas the sites can be further reinforced with carbon-13. R1=alkyl or H; m=1-10; n=1-5, where at each bis-allylic position, both Y atoms are deuterium atoms, for example,

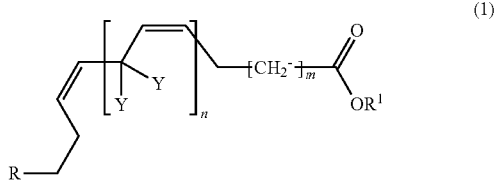

R = H, C$_3$H$_7$; R$^1$ = H, alkyl; Y = D (1)

11,11-Dideutero-cis,cis-9,12-Octadecadienoic acid (11,11-Dideutero-(9Z,12Z)-9,12-Octadecadienoic acid; D2-LA); and 11,11,14,14-Tetradeutero-cis, cis, cis-9,12,15-Octadecatrienoic acid (11,11,14,14-Tetradeutero-(9Z,12Z,15Z)-9,12,15-Octadecatrienoic acid; D4-ALA). In some embodiments, said positions, in addition to deuteration, can be further reinforced by carbon-13, each at levels of isotope abundance above the naturally-occurring abundance level. All other carbon-hydrogen bonds in the PUFA molecule may optionally contain deuterium and/or Carbon-13 at, or above, the natural abundance level.

Essential PUFAs are biochemically converted into higher homologues by desaturation and elongation. Therefore, some sites which are not bis-allylic in the precursor PUFAs will become bis-allylic upon biochemical transformation. Such sites then become sensitive to enzymatic oxidation or oxidation by ROS. In a further embodiment, such pro-bis-allylic sites, in addition to existing bis-allylic sites are reinforced by isotope substitution as shown below. Accordingly, this aspect of the invention provides for the use of compounds of Formula (2), where at each bis-allylic position, and at each pro-bis-allylic position, both X or both Y atoms may be deuterium atoms. R1=alkyl or H; m=1-10; n=1-5; p=1-10.

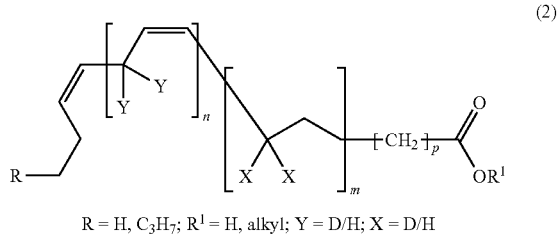

R = H, C$_3$H$_7$; R$^1$ = H, alkyl; Y = D/H; X = D/H (2)

Said positions, in addition to deuteration, can be further reinforced by carbon-13, each at levels of isotope abundance above the naturally-occurring abundance level. All other carbon-hydrogen bonds in the PUFA molecule may contain optionally deuterium and/or carbon-13 at or above the natural abundance level.

Oxidation of PUFAs at different bis-allylic sites gives rise to different sets of products upon enzymatic- or ROS-driven oxidation. For example, 4-HNE is formed from n-6 PUFAs whereas 4-HHE is formed from n-3 PUFAs (Negre-Salvayre A, et al. *Brit. J. Pharmacol.* 2008; 153:6-20). The products of such oxidation possess different regulatory, toxic, signalling, etc. properties. It is therefore desirable to control the relative extent of such oxidations. Accordingly, some aspects of the invention provide for the use of compounds of Formula (3), differentially reinforced with heavy stable isotopes at selected bis-allylic or pro-bis-allylic positions, to control the relative yield of oxidation at different sites, as shown below, such that any of the pairs of Y$^1$-Y$^n$ and/or X$^1$-X$^m$ at the bis-allylic or pro-bis-allylic positions of PUFAs are Deuterium atoms. R1=alkyl or H; m=1-10; n=1-6; p=1-10

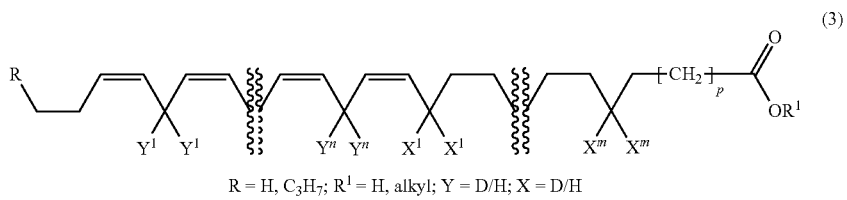

R = H, C$_3$H$_7$; R$^1$ = H, alkyl; Y = D/H; X = D/H

Said positions, in addition to deuteration, can be further reinforced by carbon-13. All other carbon-hydrogen bonds in the PUFA molecule may contain deuterium at, or above the natural abundance level. It will be appreciated that the break lines in the structure shown above represents a PUFA with a varying number of double bonds, a varying number of total carbons, and a varying combination of isotope reinforced bis-allylic and pro-bis-allylic sites.

Exact structures of compounds illustrated above are shown below that provide for both isotope reinforced n-3 (omega-3) and n-6 (omega-6) essential polyunsaturated fatty acids, and the PUFAs made from them biochemically by desaturation/elongation, to be used to slow oxidation. The PUFAs are isotope reinforced at oxidation sensitive sites. R may be H or alkyl; * represents either $^{12}$C or $^{13}$C.

D-Linoleic acids include:

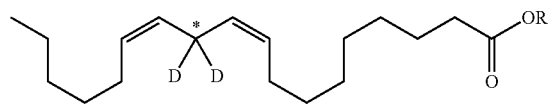

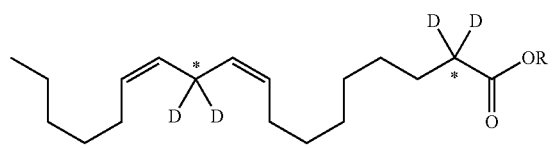

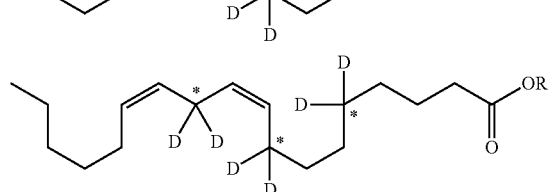

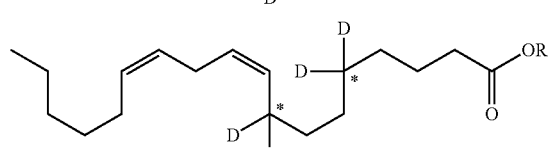

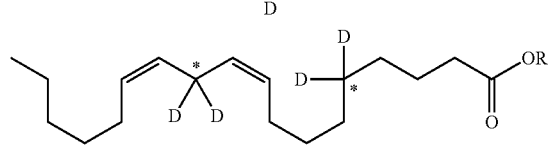

The per-deuterated linoleic acid below may be produced by microbiological methods, for example by growing in media containing D and 13C.

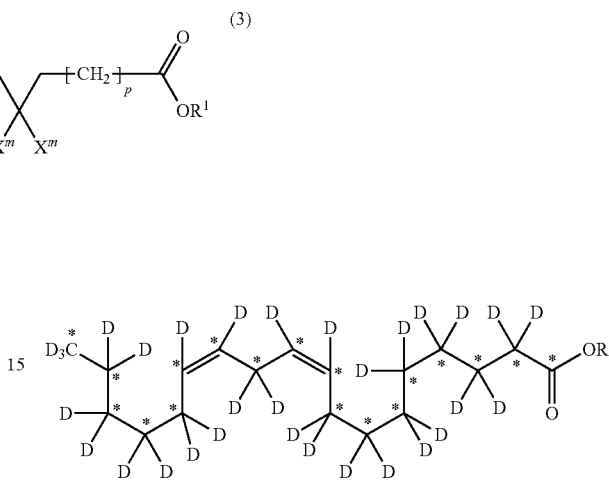

D-Arachidonic acids include:

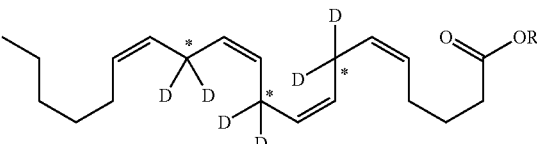

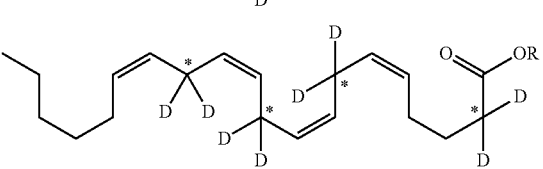

The per-deuterated arachidonic acid below may be produced by microbiological methods, such as by growing in media containing D and 13C.

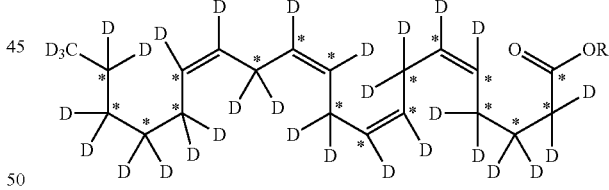

D-Linolenic acid include:

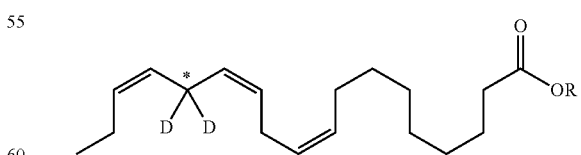

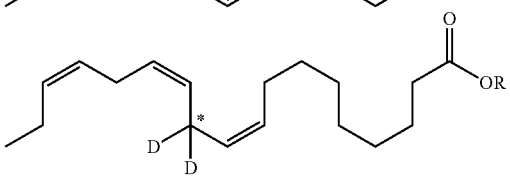

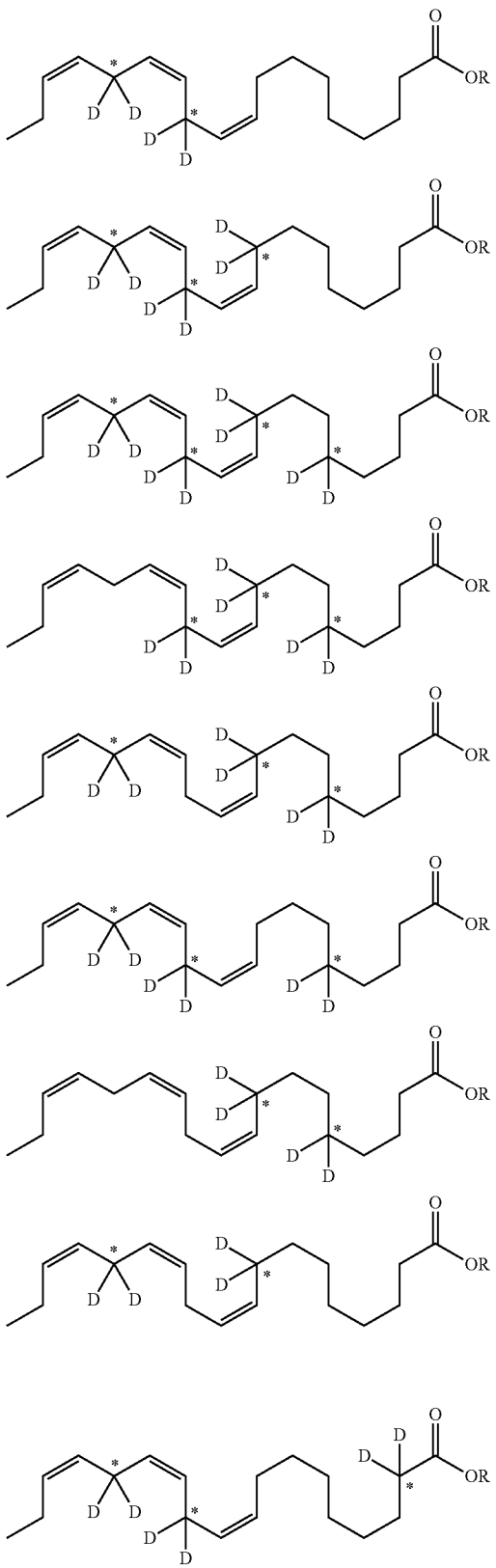

Per-deuterated linolenic acid below may be produced by microbiological methods, such as growing in media containing D and 13C.

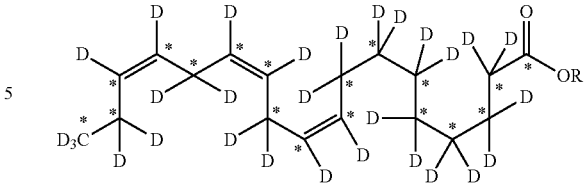

In some aspects of the invention, any PUFAs, whether essential or not, that are capable of being taken up from diet and used in the body, can be utilized. In the case of essential or non-essential PUFAs or precursors, the supplemented stabilized materials can compete with other dietary uptake and bio-manufacture to reduce the available disease-causing species concentrations.

In some aspects of the invention, the PUFAs isotopically reinforced at oxidation sensitive positions as described by way of the structures above are heavy isotope enriched at said positions as compared to the natural abundance of the appropriate isotope, deuterium and/or carbon-13.

In some embodiments, the disclosed compounds are enriched to 99% isotope purity or more. In some embodiments, the heavy isotope enrichment at said positions is between 50%-99% deuterium and/or carbon-13.

In a further embodiment of the invention, PUFAs or their essential precursors, which are isotopically reinforced at the bis-allylic positions, are used as preventive compounds against neurological diseases associated with the oxidative stress.

In a further embodiment of the invention, PUFAs or their essential precursors, which are isotopically reinforced at the bis-allylic positions, or at positions which will become bis-allylic upon biochemical desaturation, are used as preventive compounds against neurological diseases associated with the oxidative stress.

In a further embodiment of the invention, PUFAs or their essential precursors, which are isotopically reinforced at the bis-allylic positions, are used as the treatment against neurological diseases associated with the oxidative stress and AMD.

In a further embodiment of the invention, PUFAs or their essential precursors, which are isotopically reinforced at the bis-allylic positions, or at positions which will become bis-allylic upon biochemical desaturation, are used as the treatment against neurological diseases associated with the oxidative stress and AMD.

In some embodiments, the modified fatty acids, when dosed via diet as drugs or supplements, may be dosed as prodrugs as non-toxic and pharmaceutically suitable esters of the parent fatty acid or mimetic, such as an ethyl ester or glyceryl ester. This ester assists in tolerance of the drug in the gut, assists in digestion, and relies on the high levels of esterases in the intestines to de-esterify the ester pro-drugs into the active acid form of the drug which adsorbs. Hence, in some embodiments, the invention encompasses the pro-drug esters of the modified fatty acids herein. Examples of this type of drug in the market, nutrition, and clinical trials literature, including Glaxo's Lovaza, (mixtures of omega 3 fatty acid esters, EPA, DHA, and alpha-linolenic acid), Abbott's Omacor (omega-3-fatty acid esters), and most fish oil supplements (DHA and EPA esters). In some aspects, incorporation of the ester pro-drugs into tissues or cells refers to the incorporation of the modified parent PUFA as it would be used as a bodily constituent.

In some embodiments, stabilized compositions mimic natural occurring fatty acids without changing their elemental composition. For example, the substituent may retain the chemical valence shell. Some embodiments include naturally occurring fatty acids, mimetics, and their ester pro-drugs, that are modified chemically to be effective at preventing specific disease mechanisms, but are modified in a way (such as isotopic substitution) that does not change the elemental composition of the material. For example, deuterium is a form of the same element hydrogen. In some aspects, these compounds maintain elemental composition and are stabilized against oxidation. Some compounds that are stabilized against oxidation are stabilized at oxidation sensitive loci. Some compounds are stabilized against oxidation via heavy isotope substitution, then at bis-allylic carbon hydrogen bonds, etc.

In some aspects, the present composition does not include compounds disclosed in U.S. application Ser. No. 12/281,957.

In a further embodiment, oxidation-prone bis-allylic sites of PUFAs can be protected against hydrogen abstraction by moving bis-allylic hydrogen-activating double bonds further apart, thus eliminating the bis-allylic positions while retaining certain PUFA fluidity as shown below. These PUFA mimetics have no bis-allylic positions.

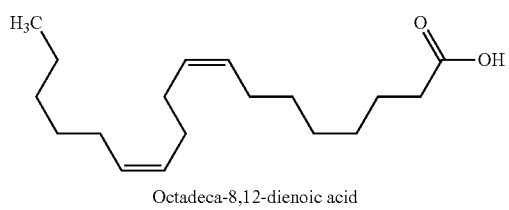

Octadeca-8,12-dienoic acid

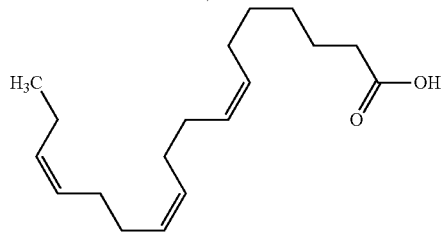

Octadeca-7,11,15-trienoic acid

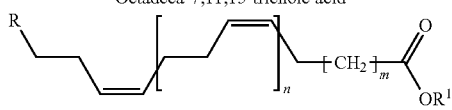

R = H, C$_3$H$_7$; R$^1$ = H; alkyl; n = 1-4; m = 1-12

In a further embodiment, oxidation-prone bis-allylic sites of PUFAs can be protected against hydrogen abstraction by using heteroatoms with valence II, thus eliminating the bis-allylic hydrogens as shown below. These PUFA mimetics also have no bis-allylic hydrogens.

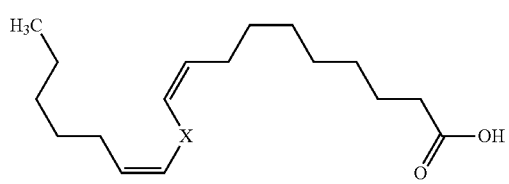

X = S: 10-Hept-1-enylsulfanyl-dec-9-enoic acid
X = O: 10-Hept-1-enyloxy-dec-9-enoic acid

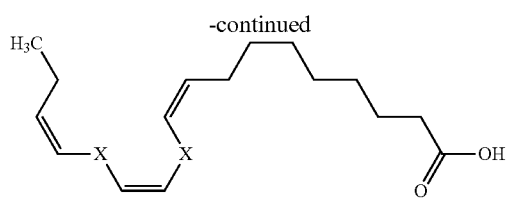

X = S: 10-(2-But-1-enylsulfanyl-vinylsulfanyl)-dec-9-enoic acid
X = O: 10-(2-But-1-enyloxy-vinyloxy)-dec-9-enoic acid

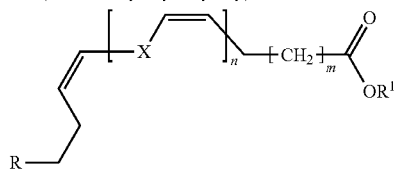

R = H, C$_3$H$_7$; R$^1$ = H; alkyl; X = O; S; n = 1-5; m = 1-12

In a further embodiment, PUFA mimetics, i.e. compounds structurally similar to natural PUFAs but unable to get oxidized because of the structural differences, can be employed for the above mentioned purposes. Oxidation-prone bis-allylic sites of PUFAs can be protected against hydrogen abstraction by di-methylation as shown below. These PUFA mimetics are dimethylated at bis-allylic sites.

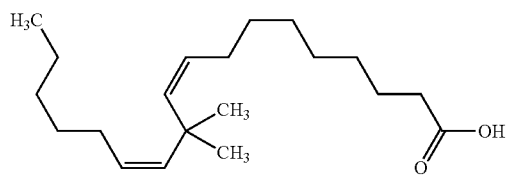

11,11-Dimethyl-octadeca-9,12-dienoic acid

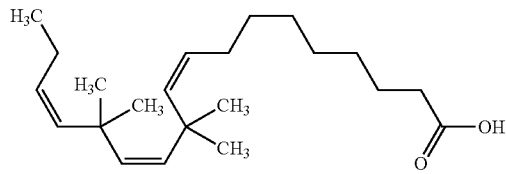

11,11,14,14-Tetramethyl-octadeca-9,12,15-trienoic acid

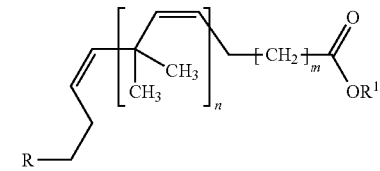

R = H, C$_3$H$_7$; R$^1$ = H; alkyl; n = 1-5; m = 1-12

In a further embodiment, oxidation-prone bis-allylic sites of PUFAs can be protected against hydrogen abstraction by alkylation as shown below. These PUFA mimetics are dialkylated at bis-allylic sites.

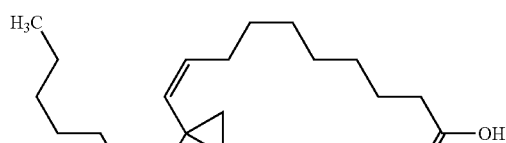

10-(1-Hept-1-enyl-cyclopropyl)-dec-9-enoic acid

-continued

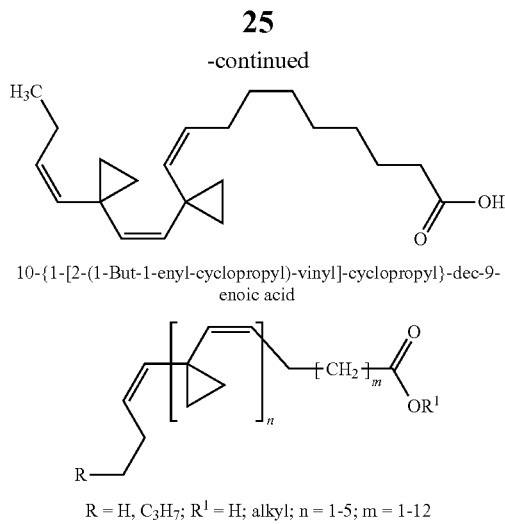

10-{1-[2-(1-But-1-enyl-cyclopropyl)-vinyl]-cyclopropyl}-dec-9-enoic acid

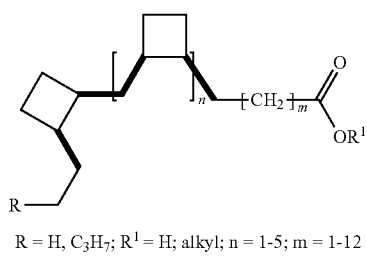

R = H, C$_3$H$_7$; R$^1$ = H; alkyl; n = 1-5; m = 1-12

In a further embodiment, cyclopropyl groups can be used instead of double bonds, thus rendering the acids certain fluidity while eliminating the bis-allylic sites as shown below. These PUFA mimetics have cyclopropyl groups instead of double bonds.

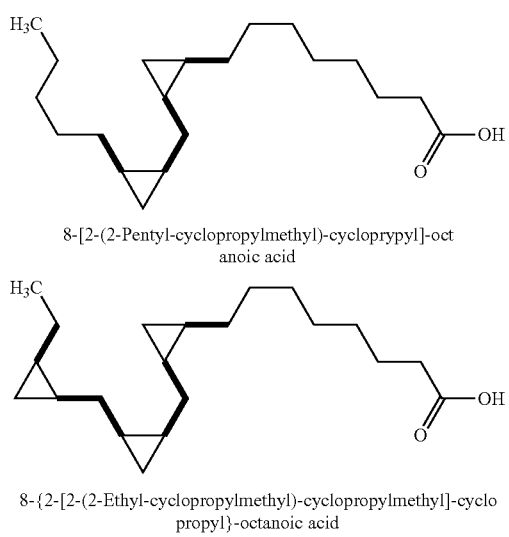

8-[2-(2-Pentyl-cyclopropylmethyl)-cycloprypyl]-octanoic acid

8-{2-[2-(2-Ethyl-cyclopropylmethyl)-cyclopropylmethyl]-cyclopropyl}-octanoic acid R = H, C$_3$H$_7$; R$^1$ = H; alkyl; n = 1-5; m = 1-12

In a further embodiment, 1,2-substituted cyclobutyl groups in appropriate conformation can be used instead of double bonds, thus rendering the acids certain fluidity while eliminating the bis-allylic sites as shown below. These PUFA mimetics have 1,2-cyclobutyl groups instead of double bonds.

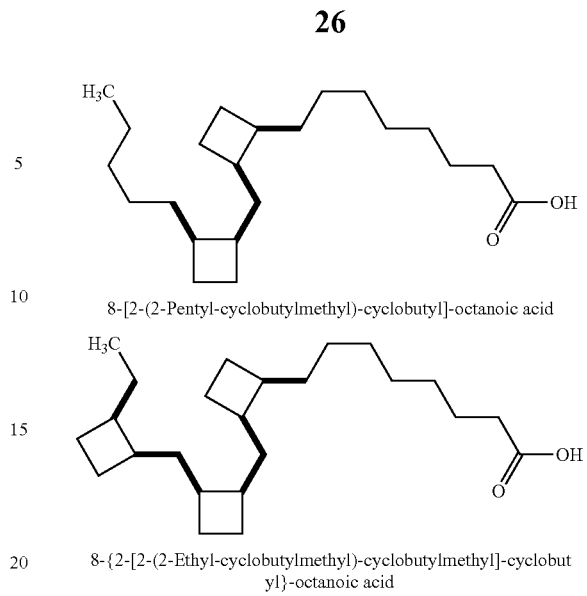

8-[2-(2-Pentyl-cyclobutylmethyl)-cyclobutyl]-octanoic acid

8-{2-[2-(2-Ethyl-cyclobutylmethyl)-cyclobutylmethyl]-cyclobutyl}-octanoic acid

R = H, C$_3$H$_7$; R$^1$ = H; alkyl; n = 1-5; m = 1-12

In a modification of the previous embodiment of mimetics with 1,2-cyclobutyl groups instead of double bonds, 1,3-substituted cyclobutyl groups in appropriate conformation can be used instead of double bonds, thus rendering the acids certain fluidity while eliminating the bis-allylic sites. The following PUFA mimetics have 1,3-cyclobutyl groups instead of double bonds.

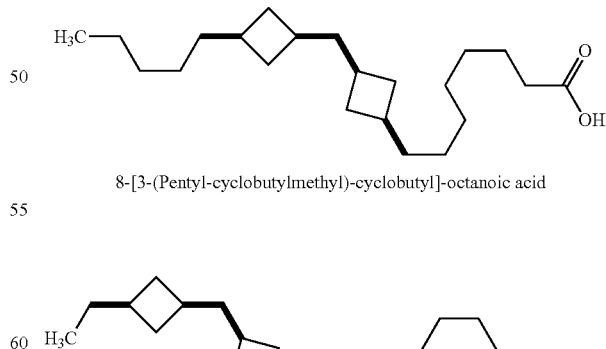

8-[3-(Pentyl-cyclobutylmethyl)-cyclobutyl]-octanoic acid

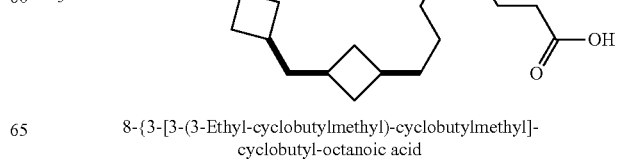

8-{3-[3-(3-Ethyl-cyclobutylmethyl)-cyclobutylmethyl]-cyclobutyl-octanoic acid

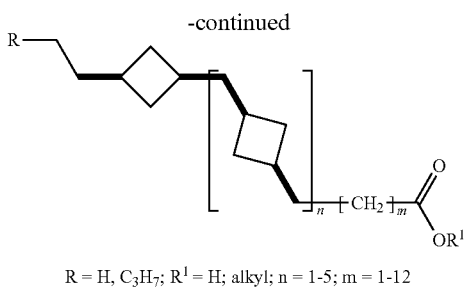

R = H, C₃H₇; R¹ = H; alkyl; n = 1-5; m = 1-12

Compounds in some aspects of the invention are expected to be taken up by neuronal cells and tissues under appropriate conditions, as is described (Rapoport S I, et al. *J. Lipid Res.* 2001; 42:678-685), and so will be useful for protecting those cells or tissues against oxidative stress.

The delivery of the reinforced PUFAs or their precursors could be through a modified diet. Alternatively, the reinforced PUFAs or their precursors can be administered as foods or food supplements, on their own or as complexes with 'carriers', including, but not limited to, complexes with albumin.

Other methods of delivering the reinforced PUFAs or their precursors, such as methods typically used for drug delivery and medication delivery, can also be employed. These methods include, but are not limited to, peroral delivery, topical delivery, transmucosal delivery such as nasal delivery, nasal delivery through cribriform plate, intravenous delivery, subcutaneous delivery, inhalation, or through eye drops.

Targeted delivery methods and sustained release methods, including, but not limited to, the liposome delivery method, can also be employed.

A further aspect of the invention provides for the use of a compound according to Formulae (1-3) and the compounds illustrated above for the treatment of AMD and neurological diseases with oxidative stress etiology.

It is contemplated that the isotopically modified compounds described herein may be administered over a course of time, in which the cells and tissues of the subject will contain increasing levels of isotopically modified compounds over the course of time in which the compounds are administered.

It may be unnecessary to substitute all isotopically unmodified PUFAs, such as nondeuterated PUFAs, with isotopically modified PUFAs such as deuterated PUFAs. In some embodiments, is preferable to have sufficient isotopically modified PUFAs such as D-PUFAs in the membrane to prevent unmodified PUFAs such as H-PUFAs from sustaining a chain reaction of self-oxidation. During self-oxidation, when one PUFA oxidises, and there is a non-oxidised PUFA in the vicinity, the non-oxidised PUFA can get oxidised by the oxidised PUFA. This may also be referred to as autooxidation. In some instances, if there is a low concentration, for example "dilute" H-PUFAs in the membrane with D-PUFAs, this oxidation cycle may be broken due to the distance separating H-PUFAs. In some embodiments, the concentration of isotopically modified PUFAs is present in a sufficient amount to maintain autooxidation chain reaction. To break the autooxidation chain reaction, for example, 1-60%, 5-50%, or 15-35% of the total molecules of the same type are in the membrane. This may be measured by IRMS (isotope ratio mass spectrometry).

A further aspect of the invention provides a dietary, supplementary or pharmaceutical composition of the active compounds.

Compositions containing the active ingredient may be in a form suitable for oral use, for example, as tablets, troches, lozenges, aqueous or oily suspensions, oil-in-water emulsions, dispersible powders or granules, emulsions, hard or soft capsules, or syrups or elixirs. Such compositions may contain excipients such as bulking agents, solubilization agents, taste masking agents, stabilisers, colouring agents, preservatives and other agents known to those ordinarily skilled in the art of pharmaceutical formulation. In addition, oral forms may include food or food supplements containing the compounds described herein. In some embodiments supplements can be tailor-made so that one type of PUFA, such as omega-3 or omega-6 fatty acids can be added to food or used as a supplement depending on the dominant fat that the food or the subject's diet contains. Moreover, compositions can be tailor-made depending on the disease to be treated. For example, an LDL related condition may require more D-linoleic acid because cardiolipin, which is made of linoleic acid, is oxidized. In other embodiments, such as retinal disease and neurological/CNS conditions may require more omega-3 fatty acids such as D-linolenic acid, because D-omega-3 fatty acids are more relevant for treating these diseases. In some aspects, when the disease is associated with HNE, then D-omega-6 fatty acids should be prescribed, whereas for HHE, D-omega-3 fatty acids should be prescribed.

Compositions may also be suitable for delivery by topical application, as a spray, cream, ointment, lotion, or as a component or additive to a patch, bandage or wound dressing. In addition the compound can be delivered to the site of the disease by mechanical means, or targeted to the site of the disease through the use of systemic targeting technologies such as liposomes (with or without chemical modification that provides them with affinity for the diseased tissue), antibodies, aptamers, lectins, or chemical ligands such as albumin, with affinity for aspects of the diseased tissue that are less abundant or not present on normal tissue. In some aspects, topical application of cosmetics may include the use of a carrier which is an isotopically modified compound or mimetic described herein for delivering through skin such as by a patch. Eye disorders may be treated with eyedrops.

A pharmaceutical composition may also be in a form suitable for administration by injection. Such compositions may be in the form of a solution, a suspension or an emulsion. Such compositions may include stabilizing agents, antimicrobial agents or other materials to improve the function of the medicament. Some aspects of the invention also encompass dry, dessicated or freeze-dried forms of the compounds which can readily be formed or reconstituted into a solution suspension or emulsion suitable for administration by injection, or for oral or topical use. Delivery by injection may be suitable for systemic delivery, and also local delivery such as injection into the eye for treating disorders relating to the eye.

EXAMPLES

Experimental: MALDI-TOF mass-spectra were recorded on a PE-ABI Voyager Elite delayed extraction instrument. Spectra were acquired with an accelerating voltage of 25 KV and 100 ms delay in the positive ion mode. Unless otherwise specified, the ¹H NMR spectra were recorded on a Varian Gemini 200 MHz spectrometer. HPLC was carried out on a Waters system. Chemicals were from Sigma-Aldrich Chemical Company (USA), Avocado research chemicals (UK), Lancaster Synthesis Ltd (UK), and Acros Organics (Fisher Scientific, UK). Silica gel, TLC plates and solvents were from BDH/Merck. IR spectra were recorded with Vertex 70 spectrometer. $^1$H and $^{13}$C NMR spectra were obtained with a Bruker AC 400 instrument at 400 and 100 MHz respectively, in CDCl$_3$ (TMS at δ=0.00 or CHCl$_3$ at δ=7.26 for $^1$H and CHCl$_3$ at δ=77.0 for $^{13}$C as an internal standard).

Example 1. Synthesis of 11,11-D2-linoleic acid

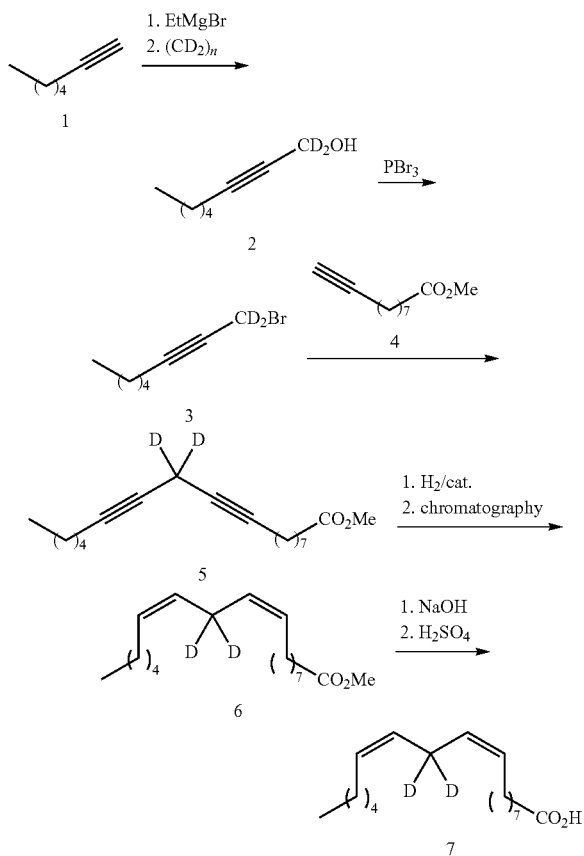

1,1-Dideutero-oct-2-yn-1-ol (2) To a solution of ethylmagnesium bromide prepared from bromoethane (100 ml), 1,2-dibromoethane (1 ml) and magnesium turnings (31.2 g) in dry THF (800 ml), heptyn-1 ((1); 170 ml) was added dropwise over 30-60 min under argon. The reaction mixture was stirred for 1 h, and then deuteroparaform (30 g) was carefully added in one portion. The reaction mixture was gently refluxed for 2 h, chilled to −10° C., and then 5-7 ml of water was slowly added. The mixture was poured into 0.5 kg slurry of crushed ice and 40 ml concentrated sulphuric acid and washed with 0.5 L of hexane. The organic phase was separated, and the remaining aqueous phase was extracted with 5:1 hexane:ethyl acetate (3×300 ml). The combined organic fraction was washed with sat. NaCl (1×50 ml), sat. NaHCO$_3$, (1×50 ml), and dried over Na$_2$SO$_4$. The solvent was evaporated in vacuo to yield 119.3 g (99%) of colourless oil which was used without further purification. HRMS, m/z calculated for C$_8$H$_{12}$D$_2$O: 128.1168; found: 128.1173. $^1$H NMR (CDCl$_3$, δ): 2.18 (t, J=7.0, 2H), 1.57 (s, 1H), 1.47 (q, J=7.0 Hz, 2H), 1.31 (m, 4H), 0.87 (t, J=7.0 Hz, 3H).

1,1-Dideutero-1-bromo-oct-2-yne (3) To a solution of (2) (3.48 g; 27.2 mmol) and pyridine (19 ml) in dry diethyl ether (300 ml), 36 ml of PBr$_3$ in 35 ml diethyl ether was added dropwise with stirring over 30 min at −15° C. under argon. The reaction mixture was allowed to gradually warm up to r.t. and then refluxed 3 h with stirring and 1 h without stirring. The reaction mixture was then cooled down to −10° C. and 500 ml of cold water was added. When the residue dissolved, saturated NaCl (250 ml) and hexane (250 ml) were added, and the organic layer was separated. The aqueous fraction was washed with hexane (2×100 ml), and the combined organic fractions were washed with NaCl (2×100 ml) and dried over Na$_2$SO$_4$ in presence of traces of hydroquinone and triethylamine. The solvent was removed by distillation at atmospheric pressure followed by rotary evaporation. The residue was fractionated by vacuum distillation (3 mm Hg) to give 147.4 g (82% counting per deutero-paraform) of pale yellow oil. B.p. 75° C. HRMS, m/z calculated for C$_8$H$_{11}$D$_2$Br: 190.0324; found: 189.0301, 191.0321. $^1$H NMR (CDCl$_3$, δ): 2.23 (t, J=7.0 Hz, 2H, CH$_2$), 1.50 (m, 2H, CH$_2$), 1.33 (m, 4H, CH$_2$), 0.89 (t, J=6.9 Hz, 3H, CH$_3$).

11,11-Dideutero-octadeca-9,12-diynoic acid methyl ester (5) CuI (133 g) was quickly added to 400 ml of DMF (freshly distilled over CaH$_2$), followed by dry NaI (106 g), K$_2$CO$_3$ (143 g). Dec-9-ynoic acid methyl ester ((4); 65 g) was then added in one portion, followed by bromide (3) (67 g). Additional 250 ml of DMF was used to rinse the reagents off the flask walls into the bulk of reaction mixture, which was then stirred for 12 h. 500 ml of saturated aqueous NH$_4$Cl was then added with stirring, followed in a few minutes by saturated aqueous NaCl and then by a 5:1 mixture of hexane:EtOAc (300 ml). The mixture was further stirred for 15 min and then filtered through a fine mesh Schott glass filter. The residue was washed with hexane:EtOAc mix several times. The organic fraction was separated, and the aqueous phase was additionally extracted (3×200 ml). The combined organic fraction was dried (Na$_2$SO$_4$), traces of hydroquinone and diphenylamine were added, and the solvent was evaporated in vacuo. The residue was immediately distilled at 1 mm Hg, to give 79 g (77%) of a 165-175° C. boiling fraction. HRMS, m/z calculated for C$_{19}$H$_{28}$D$_2$O$_2$: 292.2369; found: 292.2365. $^1$H NMR (CDCl$_3$, δ): 3.67 (s, 3H,OCH$_3$), 2.3 (t, J=7.5 Hz, 2H, CH$_2$), 2.14 (t, J=7.0 Hz, 4H, CH$_2$), 1.63 (m, 2H, CH$_2$), 1.47 (m, 4H, CH$_2$), 1.3 (m, 10H, CH$_2$), 0.88 (t, J=7.0 Hz, 3H, CH$_3$).

11,11-Dideutero-cis,cis-octadeca-9,12-dienoic acid methyl ester (6) A suspension of nickel acetate tetrahydrate (31.5 g) in 96% EtOH (400 ml) was heated with stirring to approx. 50-60° C. until the salt dissolved. The flask was flushed with hydrogen, and then 130 ml of NaBH$_4$ solution, (prepared by a 15 min stirring of NaBH$_4$ suspension (7.2 g) in EtOH (170 ml) followed by filtering) was added dropwise over 20-30 min with stirring. In 15-20 min ethylenediamine (39 ml) was added in one portion, followed in 5 min by an addition of (5) (75 g) in EtOH (200 ml). The reaction mixture was very vigorously stirred under hydrogen (1 atm). The absorption of hydrogen stopped in about 2 h. To the reaction mixture, 900 ml of hexane and 55 ml of ice cold AcOH were added, followed by water (15 ml). Hexane (400 ml) was added, and the mixture was allowed to separate. Aqueous fractions were extracted by 5:1 mix of hexane: EtOAc. The completion of extraction was monitored by TLC. The combined organic phase was washed with diluted solution of H$_2$SO$_4$, followed by saturated NaHCO$_3$ and saturated NaCl, and then dried over Na$_2$SO$_4$. The solvent was removed at reduced pressure. Silica gel (Silica gel 60, Merck; 162 g) was added to a solution of silver nitrate (43 g) in anhydrous MeCN (360 ml), and the solvent removed on a rotavap. The obtained impregnated silica gel was dried for 3 h at 50° C. (aspiration pump) and then 8 h on an oil pump. 30 g of this silica was used per gram of product. The reaction mixture was dissolved in a small volume of hexane and applied to the silver-modified silica gel, and pre-washed with a 1-3% gradient of EtOAc. When the non-polar contaminants were washed off (control by TLC), the product was eluted with 10% EtOAc and the solvent evaporated in vacuo to give 52 g of the title ester (6) as a colourless liquid. HRMS, m/z calculated for $C_{19}H_{32}D_2O_2$: 296.2682; found: 296.2676. IR(CCl$_4$): $\tilde{v}$=1740 cm$^{-1}$. $^1$H NMR (CDCl$_3$, δ): 5.32 (m, 4H), 3.66 (s, 3H, OCH$_3$), 2.29 (t, J=7.5 Hz, 2H, CH$_2$), 2.02 (m, 4H, CH$_2$), 1.60 (m, 2H, CH$_2$), 1.30 (m, 14H, CH$_2$), 0.88 (t, J=7.0 Hz, 3H, CH$_3$).

11,11-Dideutero-cis,cis-octadeca-9,12-dienoic acid (7) A solution of KOH (46 g) in water (115 ml) was added to a solution of ester (6) (46 g) in MeOH (60 ml). The reaction mixture was stirred at 40-50° C. for 2 h (control by TLC) and then diluted with 200 ml of water. Two thirds of the solvent were removed (rotavap). Diluted sulphuric acid was added to the residue to pH 2, followed by diethyl ether with a little pentane. The organic layer was separated and the aqueous layer washed with diethyl ether with a little pentane. The combined organic fractions were washed with saturated aqueous NaCl and then dried over Na$_2$SO$_4$. The solvent was evaporated to give 43 g of (7) (99%). IR(CCl$_4$): $\tilde{v}$=1741, 1711 cm$^{-1}$.

Example 2. Synthesis of 11,11,14,14-D4-linolenic acid

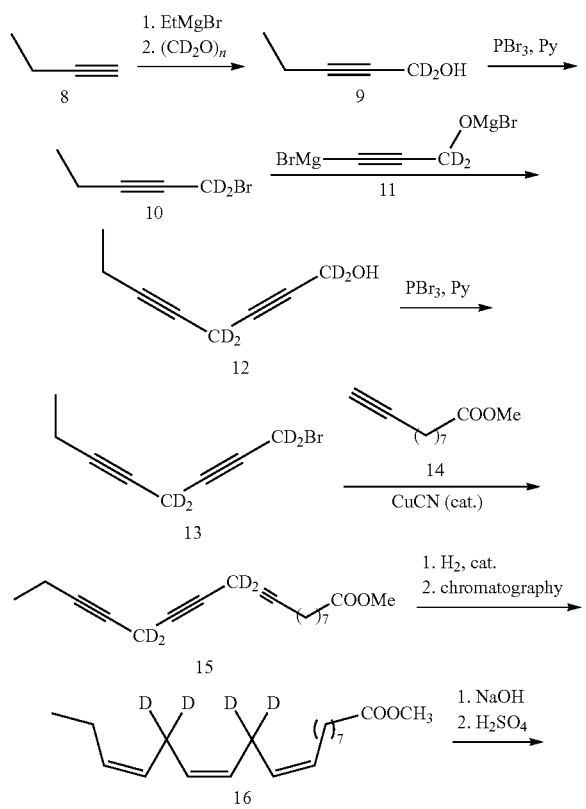

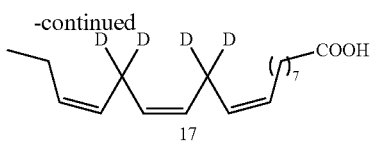

1,1-Dideutero-pent-2-yn-1-ol (9) But-1-yne (8) was slowly bubbled through a solution of ethylmagnesium bromide prepared from bromoethane (100 ml) and magnesium turnings (31.3 g) in dry THF (800 ml) on a bath (−5° C.). Every now and then the bubbling was stopped and the cylinder with but-1-yne was weighed to measure the rate of consumption. The supply of alkyne was stopped shortly after a voluminous precipitate formed (the measured mass of alkyne consumed was 125 g). The reaction mixture was warmed up to r.t. over 30 min, and then stirred for 15 min. The mixture was then heated up to 30° C., at which point the precipitate dissolved, and then stirred at r.t. for another 30 min. Deuteroparaform (28 g) was added in one portion and the mixture was refluxed for 3 h, forming a clear solution. It was cooled down to r.t. and poured into a mixture of crushed ice (800 g) and 50 ml conc. H$_2$SO$_4$. Hexane (400 ml) was added and the organic layer was separated. The aqueous phase was saturated with NaCl and extracted with a 4:1 mixture of hexane:EtOAc (1 L). The completion of extraction process was monitored by TLC. The combined organic phases were washed with saturated NaCl, NaHCO$_3$ and again NaCl, and dried over Na$_2$SO$_4$. The solvent was removed by distillation at the atmospheric pressure (max vapour temperature 105° C.). The residue (70.5 g; 94%) was used without further purification. HRMS, m/z calculated for $C_5H_6D_2O$: 86.0699; found: 86.0751. $^1$H NMR (CDCl$_3$, δ): 2.21 (q, J=7.5 Hz, 2H, CH$_2$), 1.93 (br s, 1H, OH), 1.12 (t, J=7.5 Hz, 3H, CH$_3$). $^{13}$C NMR (CDCl$_3$, δ): 87.7, 77.6, 13.7, 12.3 (signal of CD$_2$ is absent).

1,1-Dideutero-1-bromo-pent-2-yne (10) To a solution of (9) (70.5 g) and pyridine (16.5 ml) in dry diethyl ether (280 ml), 32.3 ml of PBr$_3$ in 50 ml diethyl ether was added dropwise with stirring over 30 min at −10° C. under argon. The reaction mixture was allowed to gradually warm up to r.t. over 1 h. A small amount of hydroquinone was added, and the mixture was then refluxed for 4.5 h. The reaction mixture was then cooled down to −10° C. and 350 ml of cold water was added. When the residue dissolved, saturated NaCl (350 ml) and hexane (300 ml) were added, and the organic layer was separated. The aqueous fraction was washed with diethyl ether (2×150 ml), and the combined organic fractions were washed with NaCl (2×50 ml) and dried over Na$_2$SO$_4$ in presence of traces of hydroquinone and triethylamine. The solvent was removed at atmospheric pressure, and then the 147-155° C. boiling fraction was distilled off. Alternatively, upon reaching 100° C., the distillation at atmospheric pressure was stopped and the product distilled off at 77-84° C. (25 mm Hg). Yield: 107 g of clear liquid. HRMS, m/z calculated for $C_5H_5D_2Br$: 147.9855; found: 146.9814, 148.9835. IR(CCl$_4$): $\tilde{v}$=2251 cm$^{-1}$. $^1$H NMR (CDCl$_3$, δ): 2.23 (q, J=7.5 Hz, 2H, CH$_2$), 1.11 (t, J=7.5 Hz, 3H, CH$_3$). $^{13}$C NMR (CDCl$_3$, δ): 89.3, 74.5, 13.4, 12.6 (signal of CD$_2$ is absent).

1,1,4,4-Tetradeutero-octa-2,5-diyn-1-ol (12) Ethylmagnesium bromide, prepared from ethyl bromide (53 ml) and magnesium turnings (15.8 g) in 400 ml of dry THF, was added in small portions to 350 ml of dry THF, simultaneously with acetylene bubbling through this mixture (at approx. 25 L/h rate) with vigorous stirring. The Grignard reagent solution was fed to the mixture at approx. 10 ml per 2-5 min. When all ethylmagnesium bromide was added (after approx. 2.5 h), acetylene was bubbled through the system for another 15 min. Deuteroparaform (17.3 g) and CuCl (0.2 g) were added under argon, and the reaction mixture was refluxed without stirring for 2.5 h, until deuteroparaform dissolved, to yield a solution of (11). Ethylmagnesium bromide solution, prepared from 14.8 g magnesium and 50 ml ethyl bromide in 250 ml of dry THF, was added dropwise to the reaction mixture over 20 min. When the gas emanation ceased, a condenser was attached and 250 ml of solvent were distilled off. The reaction mixture was then cooled to 30° C., and CuCl (1.4 g) was added followed by a dropwise addition, over 15 min, of bromide (10) (69 g). The reaction mixture was then refluxed for 5 h, cooled slightly (a precipitate will form if cooling is too fast), and poured into a slurry of crushed ice (1-1.2 kg) and 40 ml concentrated $H_2SO_4$. The mixture was washed with hexane (600 ml). The organic fraction was separated, and the aqueous fraction was additionally extracted with 5:1 hexane:EtOAc (2×400 ml). The combined organic fraction was washed, with saturated NaCl, followed by saturated $NaHCO_3$ and NaCl. The bulk of the solvent was removed at atmospheric pressure in presence of traces of hydroquinone and triethylamine. The residue was flushed through 100 ml of silica gel (eluent: 7:1 hexane:EtOAc). The bulk of the solvent was removed at the atmospheric pressure, and the remainder on a rotavap. 49.5 g (85%) of the title compound obtained was used without further purification. HRMS, m/z calculated for $C_8H_6D_4O$: 126.0979; found: 126.0899. IR($CCl_4$): $\tilde{v}$=3622 cm$^{-1}$. $^1$H NMR (CDCl$_3$, δ): 2.16 (q, J=7.5 Hz, 2H, $CH_2$), 1.85 (br s, 1H, OH), 1.11 (t, J=7.5 Hz, 3H, $CH_3$). $^{13}$C NMR (CDCl$_3$, δ): 82.3, 80.4, 78.3, 72.6, 13.7, 12.2

1,1,4,4-Tetradeutero-1-bromo-octa-2,5-diyne (13) was synthesised as described for bromide (3); 2 ml of pyridine, 14 ml PBr$_3$ and 250 ml of diethyl ether was used for 54.2 g of alcohol (12). The product was purified by distillation at 4 mm Hg. Yield: 53 g (65%) of (13); b.p. 100-110° C. HRMS, m/z calculated for $C_8H_5D_4Br$: 188.0135; found: 187.0136, 189.0143. IR($CCl_4$): $\tilde{v}$=2255 cm$^{-1}$. $^1$H NMR (CDCl$_3$, δ): 2.13 (q, J=7.5 Hz, 2H, $CH_2$); 1.07 (t, J=7.5 Hz, 3H, $CH_3$). $^{13}$C NMR (CDCl$_3$, δ): 82.5, 81.8, 75.0, 72.0, 13.6, 12.2.

11,11,14,14-Tetradeutero-octadeca-8,12,15-triynoic acid methyl ester (15) was synthesised in a way similar to that described for 11,11-dideutero-octadeca-9,12-diynoic acid methyl ester (5). CuI (97 g) was quickly added to 400 ml of DMF (freshly distilled over CaH$_2$), followed by dry NaI (77.5 g), K$_2$CO$_3$ (104.5 g). Dec-9-ynoic acid methyl ester ((14); 47.5 g) was then added in one portion, followed by bromide (13) (48.5 g). Additional 250 ml of DMF was used to rinse the reagents off the flask walls into the bulk of reaction mixture, which was then stirred for 12 h. 500 ml of saturated aqueous NH$_4$Cl was then added with stirring, followed in a few minutes by saturated aqueous NaCl (300 ml) followed by a 5:1 mixture of hexane:EtOAc (300 ml). The mixture was further stirred for 15 min and then filtered through a fine mesh Schott glass filter. The residue was washed with hexane:EtOAc mix several times. The organic fraction was separated, and the aqueous phase was additionally extracted (3×200 ml). The combined organic fraction was dried (Na$_2$SO$_4$), traces of hydroquinone and diphenylamine were added, and the solvent was evaporated in vacuo. The residue was immediately distilled at 1 mm Hg, to give 45.8 g (62%) of a 173-180° C. boiling fraction. An additional crystallisation was carried out as follows. The ester (15) was dissolved in hexane (500 ml) and cooled down to −50° C. The crystals formed were washed in cold hexane. The yield of this step is 80%. HRMS, m/z calculated for $C_{19}H_{22}D_4O_2$: 290.2180; found: 290.2200. $^1$H NMR (CDCl$_3$, δ): 3.66 (s, 3H, OCH$_3$), 2.29 (t, J=7.5 Hz, 2H, $CH_2$), 2.15 (m, 4H, $CH_2$), 1.61 (m, 2H, $CH_2$), 1.47 (m, 2H, $CH_2$), 1.30 (m, 6H, $CH_2$), 1.11 (t, J=7.5 Hz, 3H, $CH_3$). $^{13}$C NMR (CDCl$_3$, δ): 174.1, 82.0, 80.6, 74.7, 74.6, 73.7, 73.0, 51.3, 33.9, 28.9, 28.6, 28.52, 28.49, 24.8, 18.5, 13.7, 12.2.

11,11,14,14-Tetradeutero-cis,cis,cis-octadeca-8,12,15-trienoic acid methyl ester (16) was synthesised in a way similar to that described for 11,11-Dideutero-cis,cis-octadeca-9,12-dienoic acid methyl ester ('6'). A suspension of nickel acetate tetrahydrate (42 g) in 96% EtOH (400 ml) was heated with stirring to approx. 50-60° C. until the salt dissolved. The flask was flushed with hydrogen, and then 130 ml of NaBH$_4$ solution, (prepared by a 15 min stirring of NaBH$_4$ suspension (7.2 g) in EtOH (170 ml) followed by filtering) was added dropwise over 20-30 min with stirring. In 15-20 min ethylenediamine (52 ml) was added in one portion, followed in 5 min by an addition of (15) (73 g) in EtOH (200 ml). The reaction mixture was very vigorously stirred under hydrogen (1 atm). The absorption of hydrogen stopped in about 2 h. To the reaction mixture, 900 ml of hexane and 55 ml of ice cold AcOH were added, followed by water (15 ml). Hexane (400 ml) was added, and the mixture was allowed to separate. Aqueous fractions were extracted by 5:1 mix of hexane:EtOAc. The completion of extraction was monitored by TLC. The combined organic phase was washed with diluted solution of H$_2$SO$_4$, followed by saturated NaHCO$_3$ and saturated NaCl, and then dried over Na$_2$SO$_4$. The solvent was removed at reduced pressure. Silica gel for purification was prepared as described for (6). 30 g of this silica was used per gram of product. The reaction mixture was dissolved in a small volume of hexane and applied to the silver-modified silica gel, and pre-washed with a 1-5% gradient of EtOAc. When the non-polar contaminants were washed off (control by TLC), the product was eluted with 10% EtOAc and the solvent evaporated in vacuo to give 42 g of the title ester (16) as a colourless liquid. HRMS, m/z calculated for $C_{19}H_{28}D_4O_2$: 296.2649; found: 296.2652. IR($CCl_4$): $\tilde{v}$=1740 cm$^{-1}$. $^1$H NMR (CDCl$_3$, δ): 5.4 (m, 6H, CH-double bond), 3.68 (s, 3H, OCH$_3$), 2.33 (t, J=7.5 Hz, 2H, $CH_2$), 2.09 (m, 4H, $CH_2$), 1.62 (m, 2H, $CH_2$), 1.33 (m, 8H, $CH_2$), 0.97 (t, J=7.5 Hz, 3H, $CH_3$). $^{13}$C NMR (CDCl$_3$, δ): 174.1, 131.9, 130.2, 128.2, 128.1, 127.7, 126.9, 51.3, 34.0, 29.5, 29.04, 29.02, 27.1, 25.5, 24.9, 20.5, 14.2.

11,11,14,14-Tetradeutero-cis,cis,cis-octadeca-8,12,15-trienoic acid (17) A solution of KOH (1.5 g, 27 mmol) in water (2.6 ml was added to a solution of ester (16) (1.00 g, 3.4 mmol) in MeOH (15 ml). The reaction mixture was stirred at 40-50° C. for 2 h (control by TLC) and then diluted with 20 ml of water. Two thirds of the solvent were removed (rotavap). Diluted sulfuric acid was added to the residue to pH 2, followed by diethyl ether with a little pentane (50 ml). The organic layer was separated and the aqueous layer washed with diethyl ether with a little pentane (3×30 ml). The combined organic fractions were washed with saturated aqueous NaCl and then dried over Na$_2$SO$_4$. The solvent was evaporated to give 0.95 g of (17) (100%). IR($CCl_4$): $\tilde{v}$=1741, 1711 cm$^{-1}$.

Example 3. Synthesis of 14,14-D2-linolenic acid

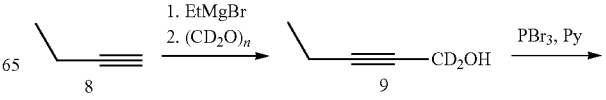

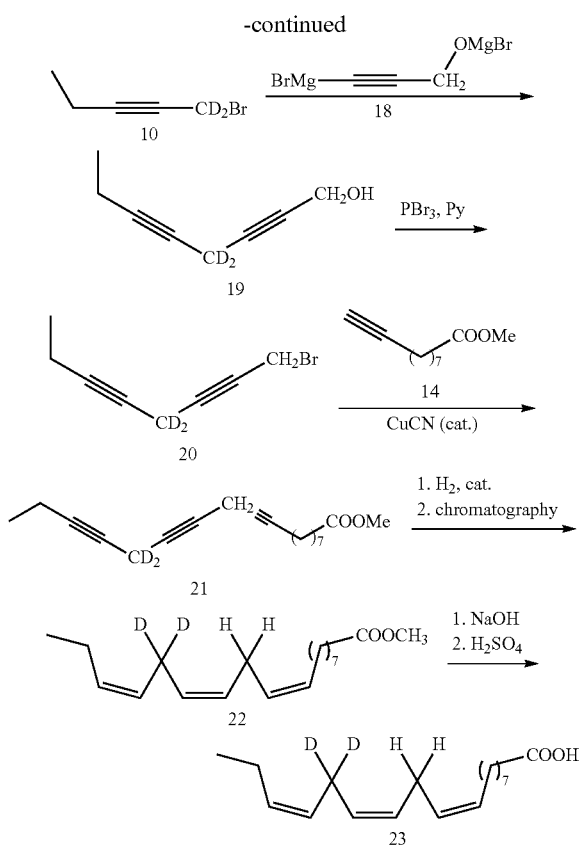

4,4-Dideutero-octa-2,5-diyn-1-ol (19) To a solution of ethylmagnesium bromide, prepared from ethyl bromide (9.2 ml, 123.4 mmol) and magnesium turnings (2.74 g, 112.8 mmol) in 40 ml of dry THF, on an ice bath with stirring, propargyl alcohol (3.16 g, 56.4 mmol) in THF (5 ml) was added dropwise over 10-15 min. The reaction mixture was allowed to warm up to r.t. and stirred for another 2 h, with occasional warming to 40° C. To thus generated dianion, 0.13 g of CuCl was added, followed by slow (over 15 min) addition of bromide (10) (6.9 g) in THF (20 ml). The reaction mixture was then stirred for 1 h at r.t. and then refluxed for 5 h. The reaction mixture was then refluxed for 5 h, cooled slightly (a precipitate will form if cooling is too fast), and poured into a slurry of crushed ice and 2.5 ml concentrated $H_2SO_4$. The mixture was washed with hexane (600 ml). The organic fraction was separated, and the aqueous fraction was additionally extracted with 5:1 hexane:EtOAc. The combined organic fraction was washed, with saturated NaCl, followed by saturated $NaHCO_3$ and NaCl, and dried over $Na_2SO_4$. The bulk of the solvent was removed at atmospheric pressure in presence of traces of hydroquinone and triethylamine. The product was purified by CC (hexane:EtOAc=15:1) to give 3.45 g (59%) of the product 19. HRMS, m/z calculated for $C_8H_8D_2O$: 124.0855; found: 124.0849. IR($CCl_4$): $\tilde{v}$=3622 $cm^{-1}$. $^1$H NMR ($CDCl_3$, δ): 4.21 (m, 2H, $CH_2$), 2.4 (m, 1H, OH), 2.16 (q, J=7.5 Hz, 2H, $CH_2$), 1.11 (t, J=7.5 Hz, 3H, $CH_3$). $^{13}$C NMR ($CDCl_3$, δ): 82.3, 80.4, 78.3, 72.6, 51.0, 13.7, 12.2.

4,4-Dideutero-1-bromo-octa-2,5-diyne (20) was synthesised as described for (3), except all solvent was removed on a rotavap. From 3.4 g (27 mmol) of (19), 3.9 g (75%) of the bromide (20) was obtained, which was used without further purification. HRMS, m/z calculated for $C_8H_7D_2Br$: 186.0011; found: 185.0019, 187.0012. IR($CCl_4$): $\tilde{v}$=2255 $cm^{-1}$. $^1$H NMR ($CDCl_3$, δ): 3.88 (br s, 2H, $CH_2$), 2.13 (q, J=7.5 Hz, 2H, $CH_2$), 1.07 (t, J=7.5 Hz, 3H, $CH_3$). $^{13}$C NMR ($CDCl_3$, δ): 82.5, 81.8, 75.0, 72.0, 14.8, 13.6, 12.2.

14,14-Dideutero-octadeca-8,12,15-triynoic acid methyl ester (21) was synthesised as described for (5). The product obtained from 9.7 g CuI, 7.8 g NaI, 10.5 g $K_2CO_3$, 4.85 g of bromide (20), 4.75 g of methyl ester (14) and 40 ml of anhydrous DMF, was purified by CC (25:1 hexane:EtOAc) to give 4.5 g (60%) of the title compound. HRMS, m/z calculated for $C_{19}H_{24}D_2O_2$: 288.2056; found: 288.2046. $^1$H NMR ($CDCl_3$, δ): 3.66 (s, 3H, $OCH_3$), 3.12 (m, 2H, $CH_2$), 2.29 (t, J=7.5 Hz, 2H, $CH_2$), 2.15 (m, 4H, $CH_2$), 1.61 (m, 2H, $CH_2$), 1.47 (m, 2H, $CH_2$), 1.30 (m, 6H, $CH_2$), 1.11 (t, J=7.5 Hz, 3H, $CH_3$). $^{13}$C NMR ($CDCl_3$, δ): 174.1, 82.0, 80.6, 74.7, 74.6, 73.7, 73.0, 51.3, 33.9, 28.9, 28.6, 28.52, 28.49, 24.8, 18.5, 13.7, 12.2, 9.7.

14,14-Dideutero-cis,cis,cis-octadeca-8,12,15-trienoic acid methyl ester (22) was synthesised as described for the linoleic acid derivative (6). For a reduction of 4.5 g of (21), 2.6 g of nickel acetate tetrahydrate and 3.2 ml ethylenediamine was used. The product was purified on $AgNO_3$-impregnated silica gel as described for (6). HRMS, m/z calculated for $C_{19}H_{30}D_2O_2$: 294.2526; found: 294.2529. IR($CCl_4$): $\tilde{v}$=1740 $cm^{-1}$. $^1$H NMR ($CDCl_3$, δ): 5.37 (m, 6H, CH-double bond), 3.68 (s, 3H, $OCH_3$), 2.82 (m, 2H, $CH_2$), 2.33 (t, J=7.5 Hz, 2H, $CH_2$), 2.09 (m, 4H, $CH_2$), 1.62 (m, 2H, $CH_2$), 1.33 (m, 8H, $CH_2$), 0.97 (t, J=7.5 Hz, 3H, $CH_3$). $^{13}$C NMR ($CDCl_3$, δ): 174.1, 131.9, 130.2, 128.2, 128.1, 127.7, 126.9, 51.3, 34.0, 29.5, 29.1, 29.04, 29.02, 27.1, 25.5, 24.9, 20.5, 14.2.

14,14-Dideutero-cis,cis,cis-octadeca-8,12,15-trienoic acid (23) To a solution of (22) (1 g, 3.4 mmol) in MeOH (15 ml), a solution of KOH (1.5 g, 27 mmol) in water (2.6 ml) was added in one portion. The reaction mixture was then processed as described for (7) to yield 0.94 g (99%) of the title acid. IR($CCl_4$): $\tilde{v}$=1741, 1711 $cm^{-1}$.

Example 4. Synthesis of 11,11-D2-linolenic acid

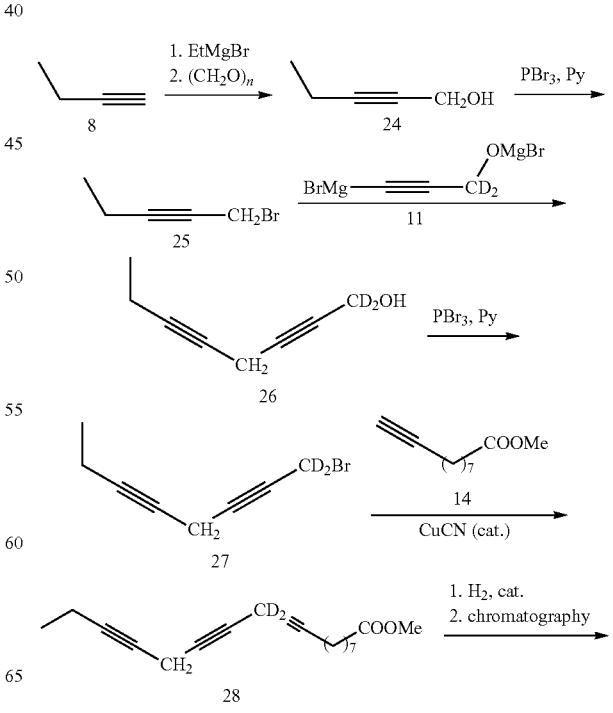

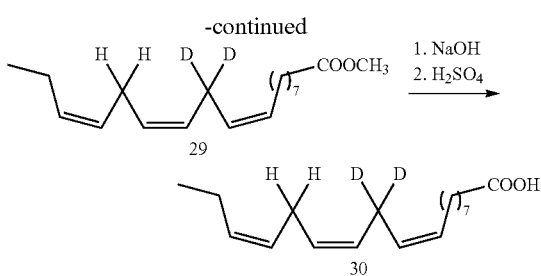

Pent-2-yn-1-ol (24) Butyn-1 ((8); 10.4 g) was bubbled through an ice-cold solution prepared from bromoethane (11.2 ml) and magnesium turnings (3.6 g) in THF (100 ml). The reaction mixture was allowed to warm up to r.t. and then stirred for 15 min. The mixture was then heated up to 30° C., at which point all precipitate dissolved. The heating was removed and the mixture stirred for another 30 min, and then paraform (3 g) was added in one portion. The reaction mixture was refluxed for 3 h (all paraform dissolved), then cooled to r.t., poured into a mixture of crushed ice (80 g) and 8 ml conc. $H_2SO_4$, and extracted with diethyl ether. The organic phase was washed with saturated $NaHCO_3$ and NaCl, and dried over $Na_2SO_4$. The solvent was removed on a rotavap, and the residue (7.56 g; 90%) was used without further purification. HRMS, m/z calculated for $C_5H_8O$: 84.0575; found: 84.0583.

1-Bromo-pent-2-yne (25) To a solution of (24) (11.7 g) and pyridine (2.66 ml) in dry diethyl ether (34 ml), 5.2 ml of $PBr_3$ in 5 ml diethyl ether was added dropwise with stirring over 30 min at −10° C. under argon. The reaction mixture was allowed to gradually warm up to r.t. over 1 h. A catalytic amount of hydroquinone was added, and the mixture was then refluxed for 4.5 h. The reaction mixture was then cooled down to −10° C. and 35 ml of cold water was added. When the residue dissolved, saturated NaCl (35 ml) and diethyl ether (30 ml) were added, and the organic layer was separated. The aqueous fraction was washed with diethyl ether (2×15 ml), and the combined organic fractions were washed with NaCl (2×400 ml) and dried over $MgSO_4$. The solvent was removed at atmospheric pressure, and then under reduced pressure (25 mm Hg), the 60-90° C. fraction was collected. Yield: 11.1 g (84%). HRMS, m/z calculated for $C_5H_7Br$: 145.9731; found: 144.9750, 146.9757.

1,1-Dideutero-octa-2,5-diyn-1-ol (26) was synthesised as described for (12) with 87% yield. HRMS, m/z calculated for $C_8H_8D_2O$: 124.0855; found: 124.0868.IR ($CCl_4$): $\tilde{v}$=3622 cm$^{-1}$. $^1$H NMR (CDCl$_3$, δ): 2.65 (m, 2H, CH$_2$), 2.4 (m, 1H, OH), 2.1 (q, 2H, CH$_2$), 1.09 (t, 3H, CH$_3$).

1,1-Dideutero-1-bromo-octa-2,5-diyne (27) was synthesised as described for (3), except all solvent was removed on a rotavap. The product was purified by distillation at reduced pressure. Yield: 86% (b.p. 100-105° C. at 4 mm Hg). (HRMS, m/z calculated for $C_8H_7D_2Br$: 186.0011; found: 184.9948, 187.9999. IR(CCl$_4$): $\tilde{v}$=2255 cm$^{-1}$. $^1$H NMR (CDCl$_3$, δ): 2.66 (m, 2H, CH$_2$), 2.1 (q, 2H, CH$_2$), 1.09 (t, 3H, CH$_3$).

11,11-Dideutero-octadeca-8,12,15-triynoic acid methyl ester (28) was synthesised as described for (5). The product obtained from 7.1 g CuI, 5.66 g NaI, 7.65 g $K_2CO_3$, 3.55 g of bromide (27), 3.47 g of methyl ester (14) and 30 ml of anhydrous DMF, was purified by CC (25:1 hexane:EtOAc) to give 3.7 g of the title compound. HRMS, m/z calculated for $C_{19}H_{24}D_2O_2$: 288.2056; found: 288.2069. $^1$H NMR (CDCl$_3$, δ): 3.7 (s, 3H, OCH$_3$), 3.15 (br. s, 2H, CH$_2$), 2.35 (m, 2H, CH$_2$), 2.17 (m, 4H, CH$_2$), 1.61 (m, 2H, CH$_2$), 1.48 (m, 2H, CH$_2$), 1.35 (m, 6H, CH$_2$), 1.11 (t, 3H, CH$_3$).

11,11-Dideutero-cis,cis,cis-octadeca-8,12,15-trienoic acid methyl ester (29) was synthesised as described for the linoleic acid derivative (6). For a reduction of 3.7 g of (28), 2.16 g of nickel acetate tetrahydrate and 2.62 ml ethylenediamine was used. The product was purified on AgNO$_3$-impregnated silica gel as described for (6) to give 1.5 g. HRMS, m/z calculated for $C_{19}H_{30}D_2O_2$: 294.2526; found: 294.2402. IR(CCl$_4$): $\tilde{v}$=1740 cm$^{-1}$. $^1$H NMR (CDCl$_3$, δ): 5.37 (m, 6H, CH-double bond), 3.6 (s, 3H, OCH$_3$), 2.82 (m, 2H, CH$_2$), 2.33 (t, o=7.5 Hz, 2H, CH$_2$), 2.09 (m 4H, CH$_2$), 1.62 (m, 2H, CH$_2$), 1.33 (m, 8H, CH$_2$), 0.97 (t, J=7.5 Hz, 3H, CH$_3$). $^{13}$C NMR (CDCl$_3$, δ): 174.1, 131.9, 130.2, 128.2, 128.1, 127.7, 126.9, 51.3, 34.0, 29.5, 29.1, 29.04, 29.02, 27.1, 25.5, 24.9, 20.5, 14.2.

11,11-Dideutero-cis,cis,cis-octadeca-8,12,15-trienoic acid (30) To a solution of (29) (1.5 g, 5.1 mmol) in MeOH (7.5 ml), a solution of KOH (1.5 g, 27 mmol) in water (3 ml) was added in one portion. The reaction mixture was then processed as described for (17) to yield 0.9 g of the title acid. IR(CCl$_4$): $\tilde{v}$=1741, 1711 cm$^{-1}$. $^1$H NMR (CDCl$_3$, δ): 11.2 (br s, 1H, COOH), 5.37 (m, 6H, CH-double bond), 2.83 (m, 2H, CH$_2$), 2.35 (t, J=7.5 Hz, 2H, CH$_2$), 2.06 (m 4H, CH$_2$), 1.63 (m, 2H, CH$_2$), 1.32 (m, 8H, CH$_2$), 0.97 (t, J=7.5 Hz, 3H, CH$_3$). $^{13}$C NMR (CDCl$_3$, δ): 180.4, 131.9, 130.2, 128.3, 128.1, 127.6, 127.1, 34.1, 29.5, 29.1, 29.03, 28.98, 27.2, 25.5, 24.6, 20.5, 14.2.

Figure 2B:
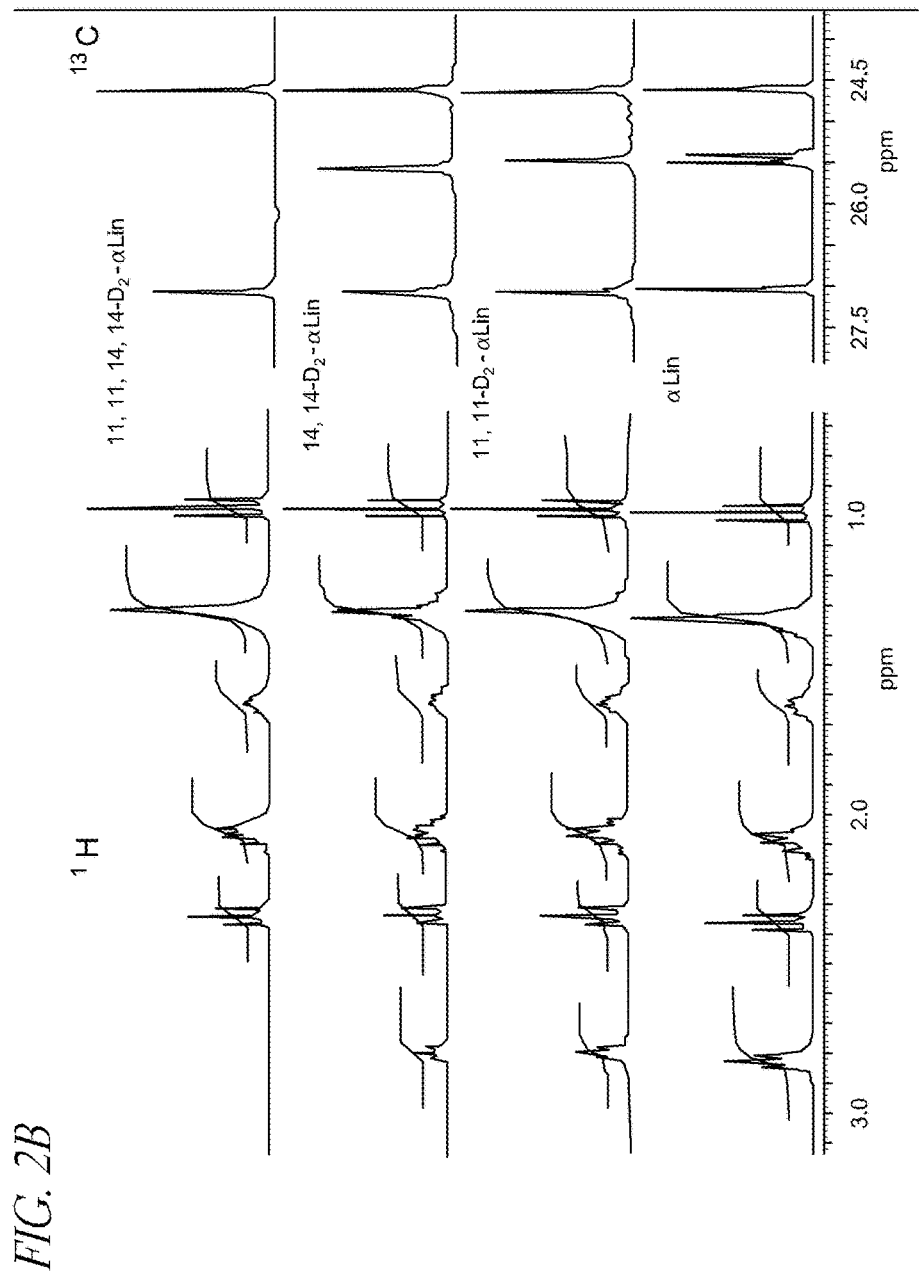

Example 5. $^1$H- and $^{13}$C-NMR analysis of deuterated PUFAs Described in Examples 1-4 (FIG. 2)

Characteristic areas of $^1$H and $^{13}$C spectra, all values in ppm. (Panel A) Deuteration of Lin acid at pos. 11 is confirmed by the disappearance of peaks in $^1$H and $^{13}$C NMR spectra. Disappearance of the peak at δ$_H$ 2.764 is expected due to absence of H atoms NMR). Disappearance of the peak at δ$_C$ 25.5 in is due to combination of Nuclear Overhauser Effect, and splitting of this particular carbon atom into a quintet by two D atoms in the deuterated form of Lin acid. (Panel B) The $^1$H NMR spectrum shows that the H atoms at C11 and C14 positions of site-specifically deuterated αLnn coincide (δ$_H$ 2.801) thus deuteration at either site (11,11-H$_2$, 14,14-D$_2$ or 11,11-D$_2$, 14,14-H$_2$) leads to a 50% decrease in integration of this peak, while deuteration of both sites (11,11,14,14-D$_4$) leads to the complete disappearance of the peak at δ$_H$ 2.801. However, $^{13}$C NMR experiments can clearly distinguish between the three deuterated forms, as the observed peaks for C11 and C14 positions are separated by a small but detectable difference. Thus, the deuteration at either C11 or C14 positions leads to disappearance of the peak at δ$_C$ 25.68 or δ$_C$ 25.60, respectively, while the deuteration at both sites leads to disappearance of the two corresponding peaks.

Example 6. Isotope Reinforcement can Shut Down PUFA Peroxidation

Q-less yeast (coq mutants) provide an ideal system to assess in vivo autoxidation of fatty acids. Coenzyme Q (ubiquinone or Q) serves as a small lipophilic antioxidant as well as an electron shuttle in the respiratory chain of the mitochondrial inner membrane. Ten *S. cerevisiae* genes (COQ1-COQ10) are required for coenzyme Q biosynthesis and function, and the deletion of any results in respiratory deficiency (Tran U C, Clarke C F. *Mitochondrion* 2007; 7S, S62). It was shown that the coq yeast mutants are exquisitely sensitive to autoxidation products of PUFAs (Do T Q et al, *PNAS USA* 1996; 93:7534-7539; Poon W W, Do T Q, Marbois B N, Clarke C F. *Mol. Aspects. Med.* 1997; 18, s121). Although *S. cerevisiae* do not produce PUFAs (Paltauf F, Daum G. *Meth. Enzymol.* 1992; 209:514-522), they are able to utilize PUFAs when provided exogenously, allowing their content to be manipulated (Paltauf F, Daum G. *Meth. Enzymol.* 1992; 209:514-522). Less than 1% of Q-less (coq2, coq3, and coq5) yeast mutants is viable following a four hour treatment with linolenic acid (Do T Q et al, *PNAS USA* 1996; 93:7534-7539; Poon W W, Do T Q, Marbois B N, Clarke C F. *Mol. Aspects. Med.* 1997; 18,s121). In contrast, 70% of wild-type (the parental genetic background is strain W303-1B) cells subjected to this treatment remain viable. The Q-less yeast are also hypersensitive to other PUFAs that readily autoxidize (such as arachidonic acid), but behave the same as the wild-type parental strain to treatment with the monounsaturated oleic acid (Do T Q et al, *PNAS USA* 1996; 93:7534-7539). The hypersensitivity of the Q-less yeast mutants is not a secondary effect of the inability to respire, because cor1 or atp2 mutant yeast (lacking either the bc1 complex or the ATP synthase, respectively) show wild-type resistance to PUFA treatment (Do T Q et al, *PNAS USA* 1996; 93:7534-7539; Poon W W, Do T Q, Marbois B N, Clarke C F. *Mol. Aspects. Med.* 1997; 18, s121).

Figure 3:
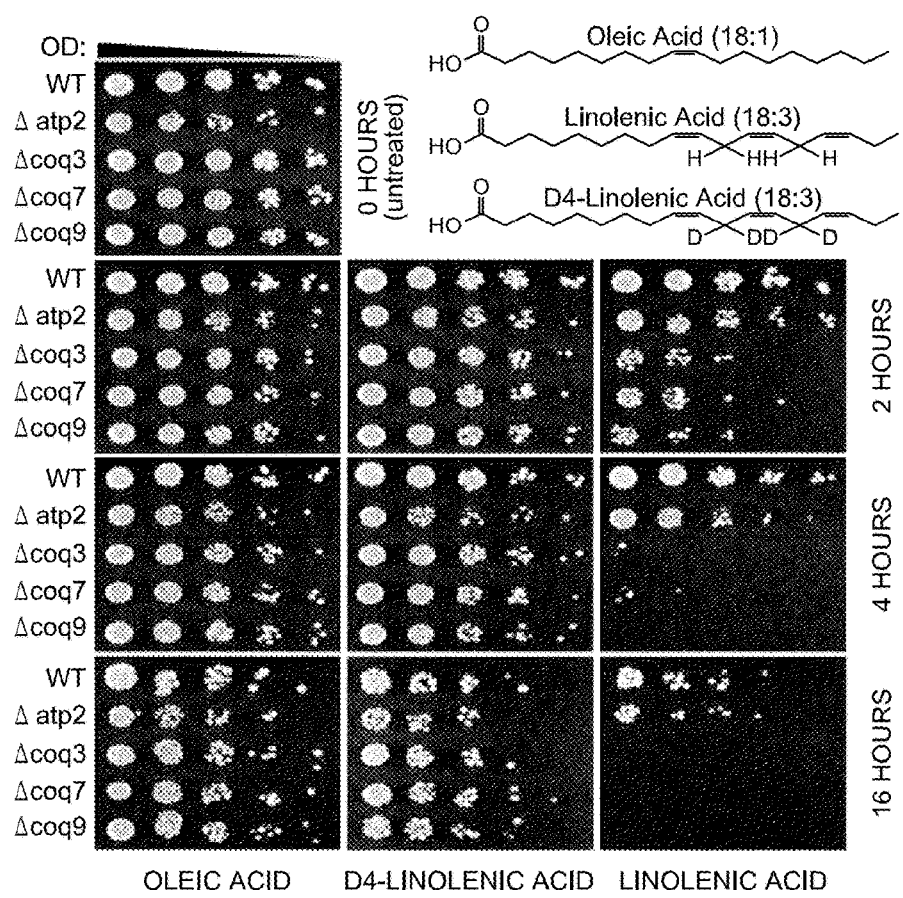
FIG. 3. Sensitivity of coq null mutants to treatment with linolenic acid is abrogated by isotope-reinforcement. Yeast coq3, coq7 and coq9 null mutants were prepared in the W303 yeast genetic background (WT). Yeast strains were grown in YPD medium (1% Bacto-yeast extract, 2% Bacto-peptone, 2% dextrose) and harvested while in log phase growth ($OD_{600nm}$=0.1-1.0). Cells were washed twice with sterile water and resuspended in phosphate buffer (0.10 M sodium phosphate, pH 6.2, 0.2% dextrose) to an $OD_{600nm}$=0.2. Samples were removed and 1:5 serial dilutions starting at 0.20 OD/ml were plated on YPD plate medium, to provide a zero time untreated control (shown in top left panel). The designated fatty acids were added to 200 uM final concentration to 20 ml of yeast in phosphate buffer. At 2 h, 4 h, and 16 h samples were removed, 1:5 serial dilutions prepared, and spotted onto YPD plate medium. Pictures were taken after 2 days of growth at 30° C. This panel is representative of two independent assays, performed on different days.

A plate dilution assay can be used to assess PUFA sensitivity. This assay can be performed by spotting serial five-fold dilutions of aliquots onto YPD plate media (FIG. 3). The sensitivity of the different strains can be observed by visual inspection of the density of cells in each spot.

Figure 4:
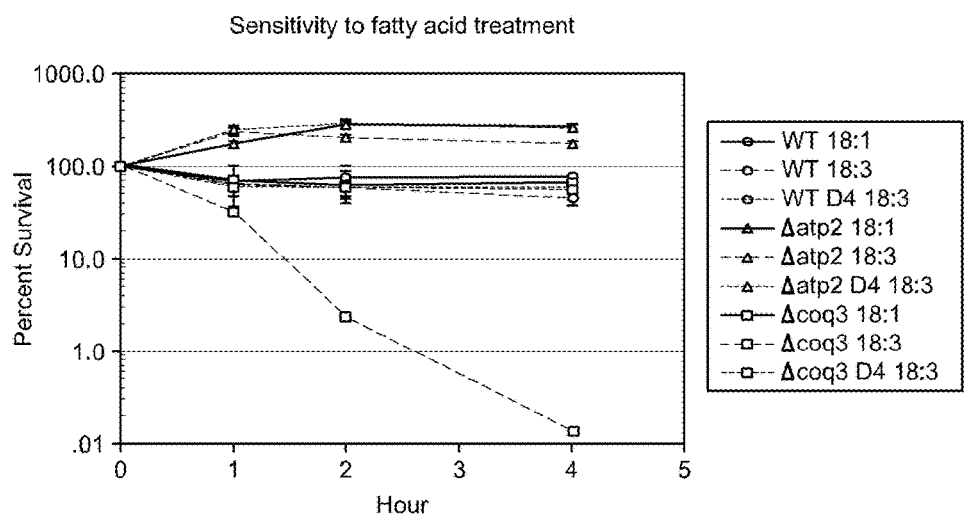
FIG. 4. Yeast coq mutants treated with isotope-reinforced D4-linolenic acid are resistant to PUFA-mediated cell killing. The fatty acid sensitive assay was performed as described in FIG. 6-1, except that 100 ul aliquots were removed at 1, 2, and 4 h and, following dilution, spread onto YPD plates. Pictures were taken after 2 to 2.5 days, and the number of colonies counted. Yeast strains include Wild type (circles), atp2 (triangles), or coq3 (squares); Fatty acid treatments include oleic C18:1 (solid line), linolenic, C18:3, n-3 (dashed line) or 11,11,14,14-D4-linolenic, C18:3, n-3, (dotted line).

Treatment with linolenic acid causes dramatic loss of viability of the coq null mutants. In stark contrast, coq mutants treated with the D4-linolenic acid were not killed, and retained viabilities similar to yeast treated with oleic acid. Quantitative colony counting revealed that the viability of cells treated with oleic and D4-linolenic was similar (FIG. 4), while the viability of the coq mutants was reduced more than 100-fold following treatment with the standard linolenic acid for 4 h. These results indicate that isotope-reinforced linolenic acid is much more resistant to autoxidation than is the standard linolenic acid, as evidenced by the resistance of the hypersensitive coq mutants to cell killing.

GC-MS can detect fatty acids and PUFAs in yeast cells. Yeast do not synthesize PUFAs, however they do incorporate exogenously supplied linoleic and linolenic acids (Avery S V, et al. *Applied Environ. Microbiol.* 1996; 62, 3960; Howlett N G, et al. *Applied Environ. Microbiol.* 1997; 63, 2971).

Figure 5:
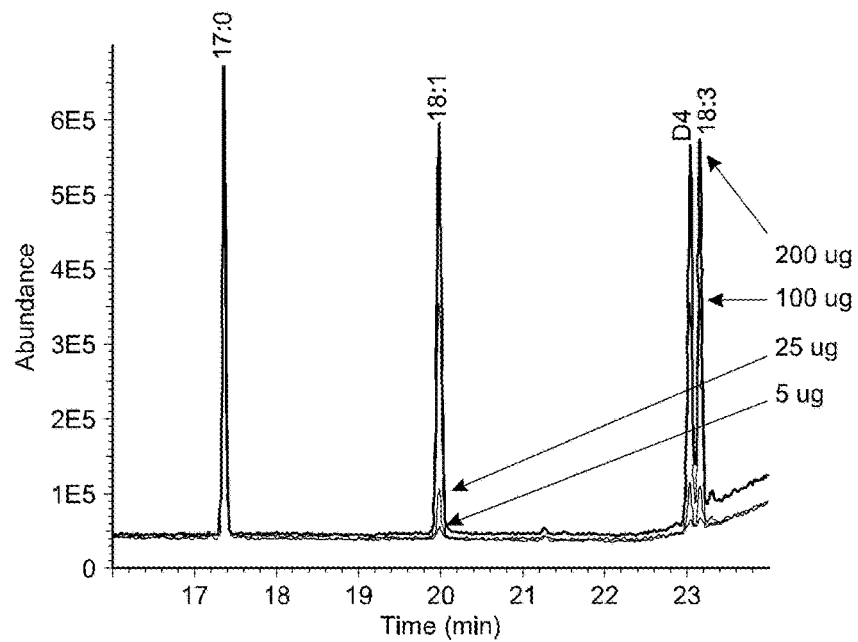
FIG. 5. Separation and detection of fatty acid methyl ester (FAME) standards by GC-MS. FAMEs were prepared as described (Moss C W, Lambert M A, Merwin W H. *Appl. Microbiol.* 1974; 1, 80-85), and the indicated amounts of free fatty acids and 200 µg of C17:0 (an internal standard) were subjected to methylation and extraction. Samples analyses were performed on an Agilent 6890-6975 GC-MS with a DB-wax column (0.25 mm×30 m×0.25-m film thickness) (Agilent, catalog 122-7031).

Therefore, it seems likely that yeast would also incorporate exogenously supplied D4-linolenic acid. However, it is possible that the differential sensitivity to linolenic and D4-linolenic might be attributed to differences in integration into the cell rather than autoxidation. To test whether this is the case, the extent of uptake of this fatty acid was monitored. First the conditions of separation of fatty acid methyl esters (FAME) of C18:1, C18:3, D4-18:3 and C17:0 (to be used as an internal standard) were determined. The GC-MS chromatogram shown in FIG. 5 establishes both separation and sensitivity of detection of these fatty acid methyl ester standards.

Figure 6:
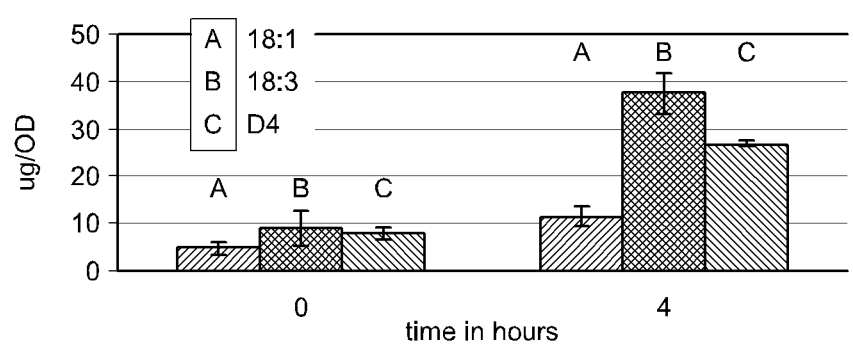
FIG. 6. Uptake of exogenously supplied fatty acids by yeast. WT (W303) yeast were harvested at log phase and incubated in the presence of 200 µM of the designated fatty acid for either 0 or 4 h. Yeast cells were harvested, washed twice with sterile water and then subjected to alkaline methanolysis and saponification, and lipid extraction as described (Moss C W, Lambert M A, Merwin W H. *Appl. Microbiol.* 1974; 1, 80-85; (Shaw, 1953 Shaw, W. H. C.; Jefferies, J. P. Determination of ergosterol in yeast. *Anal Chem* 25:1130; 1953). Each designated fatty acid is given as µg per $OD_{600nm}$ yeast, and was corrected for the recovery of the C17:0 internal standard.
Figure 7:
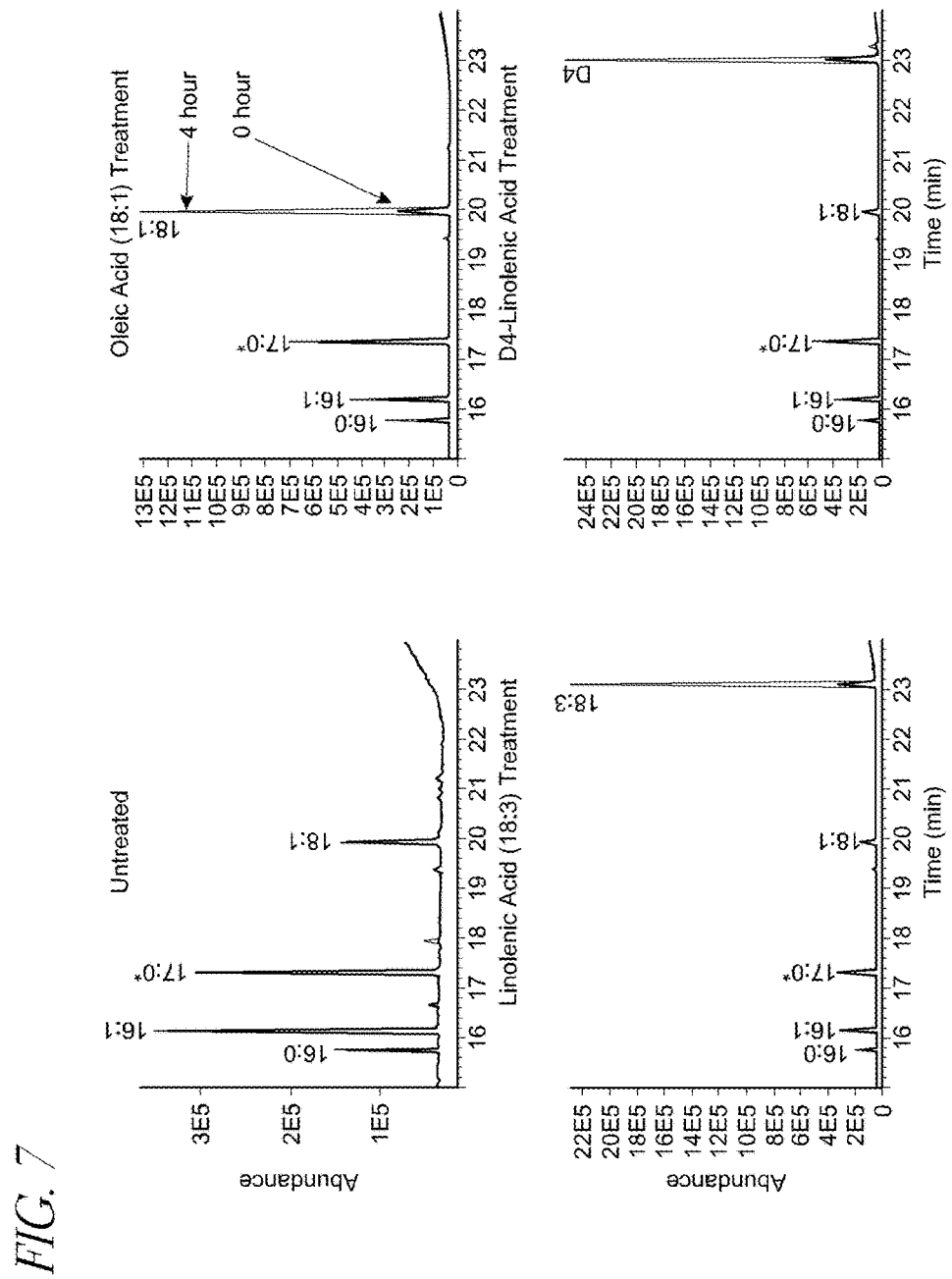
FIG. 7. Chromatograms of the yeast extracts subjected to GC-MS analyses. The different traces represent the 0 and 4 h incubations, respectively. The peak area of Each FAME (C18:1, C18:3 and D4-linolenic) was divided by the peak area of the C17:0 standard, quantified with a calibration curve. The endogenous 16:0 and 16:1 change very little, while the exogenously added fatty acids increased significantly.

Wild-type yeast were harvested during log phase growth and incubated in the presence of exogenously added fatty acid (for 0 or 4 h) in the presence of phosphate buffer plus 0.20% dextrose, as described for the fatty acid sensitivity assay. Cells were harvested, washed twice with 10 ml sterile water, and the yeast cell pellets were then processed by alkaline methanolysis as described above. The fatty acids are detected as methylesters (FAMEs) following GC-MS with C17:0 added as an internal standard (FIG. 6). The amounts of 18:3 and D4 detected after 4 h incubation were extrapolated from the calibration curve. These results indicate yeast avidly incorporate both linolenic and D4-linolenic acid during the 4 h incubation period. Based on these results, it is obvious that the enhanced resistance of the coq mutant yeast to treatment with D4-C18:3 is not due to lack of uptake.

D2-linolenic, 11,11-D2-linolenic acid and 14,14-D2-linolenic acid, were also used on this yeast model and rendered comparable protection.

Example 7. D-PUFA Mitigates Oxidative Stress and Increases Survival in Retinal Cells Implicated in AMD and Diabetic Retinopathy Pathology Several cell types, including microvascular endothelium (MVEC), retinal pigment epithelium (RPE) and retinal neurons (retinal ganglion cells) were tested for survival in cell culture. Cells were kept in the medium containing either hydrogenated (control) or deuterated D2-linoleic ($\omega$-6; LA) and D4-linolenic ($\omega$-3; ALA) acids (20 $\mu$M; ratio of $\omega$-6 to $\omega$-3: 1:1 or 2:1) for 72 hrs. The incorporation of PUFAs into cells was monitored by GC. PUFAs were shown to be readily taken up by cells according to the Table 1, showing incorporation of PUFAs into MVECs.

TABLE 1

|  |  | Area unlabelled | Area labelled | ratio |
|---|---|---|---|---|
| control | linoleate | 78392976 | 4556042 | 0.058 |
|  | linolenate | 1488866 | 149411 | 0.100 |
| PUFA | linoleate | 96026830 | 5525295 | 0.058 |
|  | linolenate | 2347729 | 113468 | 0.048 |
| Deuterated PUFA | linoleate | 34957060 | 2599969 | 0.074 |
|  | linolenate | 747128 | 134824 | 0.180 |

Figure 8:
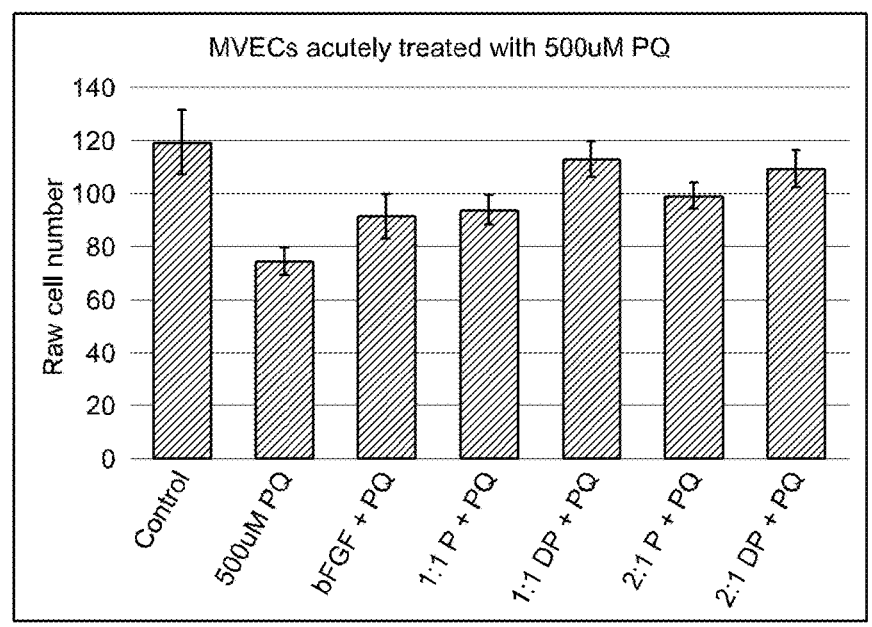
FIG. 8. Survival of H- and D-PUFA treated MVEC cells after acute intoxication by paraquat. For all cell types tested, D-PUFA had protective effect compared to controls, similar to that shown on Figure for MVEC cells.

The cells were then treated with paraquat (PQ; 500 $\mu$M), a common oxidative stress-generating compound. For survival measurement, cells were counted using haemocytometer and trypan blue exclusion method. FIG. 8 shows the survival of H— and D-PUFA treated MVEC cells after acute intoxication by paraquat. For all cell types tested, D-PUFA had protective effect compared to controls, similar to that shown on FIG. 8 for MVEC cells.

Example 8. Isotope Ratio Mass-Spectrometry Confirms Rapid Incorporation of D-PUFA into Phospholipid Membranes of Brain Tissues When delivering D2-LA and D4-ALA through dietary supplementation, incorporation into animal tissues cannot be monitored by chromatography based analytical techniques because said PUFAs can be further extended/desaturated in mammals, thus changing their chemical identity. We used an isotope ratio mass-spectrometry technique which allows for measurement of the total increase in deuterium composition in lipid membranes, thus reporting on incorporation of D2-LA, D4-ALA, and any other PUFA derived from these two. Using this method, a substantial uptake of D-PUFA into mouse brain tissue was detected. Mice were supplemented with D-PUFA or H-PUFA as the only PUFA source for 6 days, exposed acutely to 40 mg/kg MPTP ((1-methyl-4- phenyl-1,2,3,6-tetrahydropyridine) or saline vehicle and continued on the same diet for an additional 6 days. MPTP is a well-recognized model in mice of Parkinson's disease. Brains were removed and dissected, and homogenate samples from saline-treated mice were analyzed for deuterium content. The MS was calibrated with different concentrations of D2-LA and D4-ALA and compared with H-PUFA baselines (Table 2). Table 2 shows the isotope ratio mass spectrometry measurement of D-PUFA incorporation into phospholipid membranes of brain tissues.

The data are expressed as a ratio: the delta of the deuterium peak area in measured samples against the levels in Vienna standard mean ocean water (V-SMOW), an MS standard for deuterium levels, ratio of the areas of the hydrogen peaks (d D/H), in per mil (‰). D-PUFA-fed mice had deuterium levels consistent with literature references of 3-8% incorporation per day. A higher-order PUFA concentration peaks in brain within 8 hours after administration of a single dose of LA and ALA, and that LA and ALA are desaturated and elongated as needed enzymatically in the absence of higher PUFAs.

TABLE 2

Incorporation of D-PUFA into brain tissue.

| Group | d D/H |
|---|---|
| Vienna Std Mean Ocean Water | 1.0 ± 0.0 |
| H-PUFA (LA) sample | −198.8 ± 2.17 |

TABLE 2-continued

Incorporation of D-PUFA into brain tissue.

| Group | d D/H |
|---|---|
| D-PUFA sample 1 | 1703.5 ± 36.1 |
| D-PUFA sample 2 | 1838.2 ± 10.8 |
| D-PUFA sample 3 | 1973.7 ± 6.13 |

Each of the three samples above contain a mixture of 1:1 ratio of D2-linolenic acid:D4-linolenic acid.

Example 9. Toxicology Studies of Mice Supplemented with D-PUFA Reveal No Anomalies in Major Blood Biomarkers With a more protracted dosing paradigm (i.e. 3 weeks of dietary replacement), chemical analysis of blood serum of H-PUFA- and D-PUFA-supplemented mice (performed at UC Davis) revealed no difference in major biomarkers of renal function, liver function, blood lipids, etc for H-PUFA/D-PUFA saline treated mice. In this example, D-PUFA is a 2:1 mixture of D2-linoleic acid: D4-linolenic acid.

Tested parameters included measurements of triglycerides; total protein; total bilirubin; phosphorus; free fatty acids; HDL; glucose; creatine; cholesterol; calcium; blood urea nitrogen; alkaline phosphatase; albumin; aspartate aminotransferase; and others in Table 3.

TABLE 3

| Mouse ID # | Sample volume | Alanine Aminotransferase U/L | Aspartate Aminotransferase U/L | Albumin g/dl | Alkaline Phosphatase U/L | Blood Urea Nitrogen mg/dl | Calcium mg/dl | Cholesterol mg/dl | Creatinine mg/dl |
|---|---|---|---|---|---|---|---|---|---|
| 4 | 100 | 273.0 | 3008.7 | 3.09 | 81.7 | 19.1 | 7.96 | 148.3 | 0.189 |
| 5 | 110 | 5726.7 | 8478.9 | 3.42 | 31.1 | 25.4 | 7.40 | 185.1 | 0.356 |
| 7 | 100 | 156.0 | 1470.6 | 2.82 | 35.1 | 18.9 | 7.64 | 151.2 | 0.154 |
| 10 | 60 | 518.4 | 4653.0 | 3.02 | QNS | 20.1 | 6.78 | 184.0 | 0.151 |
| 11 | 70 | 144.0 | 1635.3 | 3.63 | 72.7 | 20.3 | 8.75 | 170.8 | 0.179 |
| 13 | 14 | 3518.1 | 15669.0 | QNS | <0.1 | 31.5 | QNS | 166.5 | 1.126 |
| 14 | 75 | 216.9 | 2107.8 | 3.03 | 42.4 | 24.4 | 7.46 | 173.6 | 0.170 |
| 25 | 75 | 589.5 | 4707.0 | 3.20 | 18.8 | 18.0 | 5.97 | 193.4 | 0.126 |
| 27 | 100 | 727.2 | 6015.6 | 2.63 | <0.1 | 36.2 | 5.71 | 166.7 | 1.453 |
| 28 | 100 | 468.9 | 4018.5 | 2.93 | 49.3 | 21.2 | 6.90 | 164.4 | 0.232 |
| 29 | 29 | 1898.1 | 12510.0 | QNS | QNS | 24.9 | QNS | 208.8 | 0.111 |
| 30 | 100 | 2963.7 | 5371.2 | 3.38 | 50.3 | 18.2 | 6.29 | 174.7 | 0.225 |
| Mean D-PUFA | 76 | 1508 | 5289 | 3.17 | 52.6 | 22.8 | 7.67 | 168.5 | 0.332 |
| SD D-PUFA | 33 | 2225 | 5189 | 0.30 | 23.0 | 4.6 | 0.66 | 14.5 | 0.357 |
| Mean H-PUFA | 81 | 1329 | 6524 | 3.04 | 39.5 | 23.7 | 6.22 | 181.6 | 0.429 |
| SD D-PUFA | 31 | 1078 | 3428 | 0.33 | 17.9 | 8 | 0.51 | 19.0 | 0.575 |

| Mouse ID # | Glucose mg/dl | High Density Lipoprotein mg/dl | Non-esterified Fatty Acid mEq/L | Phosphorus mg/dl | Total Bilirubin mg/dl | Total Protein g/dl | Triglyceride mg/dl |
|---|---|---|---|---|---|---|---|
| 4 | 160.2 | 104.49 | 1.08 | 13.07 | 0.185 | 5.32 | 38.9 |
| 5 | 355.6 | 134.37 | 1.07 | 18.59 | 0.275 | 6.56 | 57.9 |
| 7 | 174.6 | 107.39 | 1.11 | 10.14 | 0.192 | 5.26 | 82.7 |
| 10 | 136.5 | 138.15 | 1.06 | QNS | 0.272 | 6.07 | 46.1 |
| 11 | 107.9 | 139.86 | 1.18 | 9.33 | 0.162 | 5.72 | 33.5 |
| 13 | 176.4 | 135.09 | 0.99 | QNS | QNS | QNS | 31.5 |
| 14 | 93.3 | 47.78 | 1.06 | 10.41 | 0.235 | 6.07 | 43.8 |
| 25 | 164.5 | 147.96 | 1.01 | 18.39 | 0.269 | 6.74 | 41.0 |
| 27 | 88.3 | 98.46 | 0.87 | 24.57 | 0.301 | 6.26 | 26.9 |
| 28 | 224.9 | 50.54 | 1.02 | 14.16 | 0.231 | 5.87 | 49.6 |
| 29 | QNS | 77.58 | 0.20 | QNS | QNS | QNS | 27.9 |
| 30 | 227.4 | 131.04 | 1.17 | 21.42 | 0.349 | 6.28 | 46.7 |
| Mean D-PUFA | 172.1 | 115.30 | 1.08 | 12.31 | 0.220 | 5.83 | 47.8 |

TABLE 3-continued

|  | | | | | | | |
|---|---|---|---|---|---|---|---|
| SD D-PUFA | 87.0 | 33.21 | 0.06 | 3.78 | 0.048 | 0.50 | 17.7 |
| Mean H-PUFA | 176.3 | 101.12 | 0.85 | 19.64 | 0.288 | 6.29 | 38 |
| SD D-PUFA | 65.5 | 39.40 | 0.38 | 4.44 | 0.050 | 0.36 | 11 |

Example 10. Supplementation with D-PUFA Increases the Level of HDL, and Decreases the Level of LDL Mice supplemented with D-PUFA as the only source of dietary PUFA for 3 weeks have slightly elevated levels of HDL (115 mg/dl; Example 9) as compared to the control cohort dosed with H-PUFA (101 mg/dl). The D-PUFA cohort also has lower levels of cholesterol (158 mg/dl) comparesd to H-PUFA control group (181 mg/dl). The LDL level, i.e., the difference between cholesterol level and HDL, for the H-PUFA cohort is 80 mg/dl, or almost twice as high as compared to 43 mg/dl in the D-PUFA cohort. (D-PUFA is a 1:1 mixture of D2-linoleic acid: D4-linolenic acid.)

Figure 9:
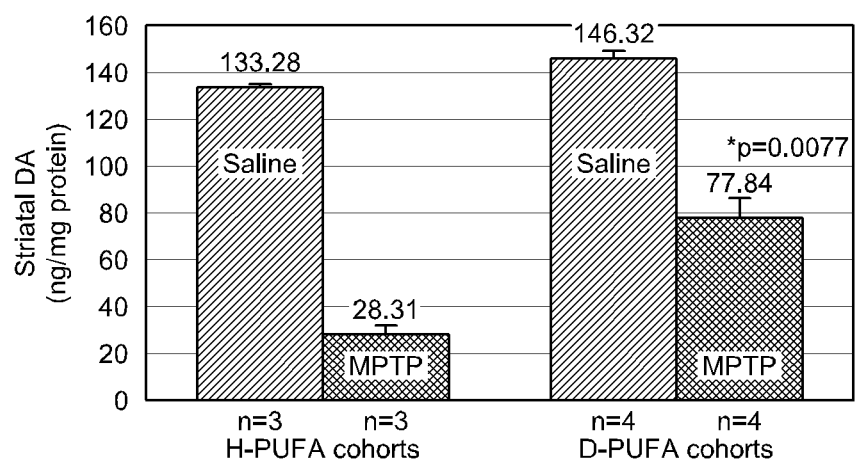
FIG. 9. D-PUFA partially attenuates MPTP-induced striatal dopamine depletion in C57BL/6 mice. Mice, aged 8 weeks, were fed fat-free diet supplemented with either D-PUFAs or H-PUFAs for 6 days, exposed to 40 mg/kg MPTP, i.p., or saline, continued on D- or H-PUFA diet and sacrificed 6 days later. Striatal dopamine was measured by HPLC. MPTP produced a robust depletion in H-PUFA-fed mice (78%) which was significantly less in the D-PUFA-fed cohort (47%).

Example 11. Mouse MPTP Model of Parkinson's Disease: D-PUFA Supplementation Protects Against Dopamine Loss Isotopic reinforcement of PUFA at bis-allylic positions prevents oxidative stress-related injury and is thus neuroprotective. Mice were fed with either D-PUFA or H-PUFA (fat-free diet (MPBio) was supplemented with 10% fat (saturated and monounsaturated (oleic acid), of which 10% (i.e. 1% of the total fat) was a mixture of LA:ALA (1:1), or D2-LA:D4-ALA (1:1)) for six days, and then challenged with MPTP or saline. Neurochemical analyses revealed striking neuroprotection of striatal dopamine with values from D-PUFA-fed mice nearly 3-fold higher: 77.8±13.1 (D-PUFA; n=4) vs. 28.3±6.3 (H-PUFA; n=3) ng/mg protein. (D-PUFA is a 1:1 mixture of D2-linolenic acid: D4-linolenic acid. A significant improvement in the level of the DA metabolite 3,4-dihydroxyphenylacetic acid (DOPAC) was also noted in the D-PUFA group, as well as striatal immunoreactivity for tyrosine hydroxylase (TH) by Western blot analysis. Importantly, in saline-treated mice, a trend in increased striatal DA level (11%) was noted in the D-PUFA- vs. H-PUFA-fed cohorts (p=0.053; FIG. 9).

Example 12. Attenuation of Alpha-Cynuclein Aggregation by D-PUFA Supplementation Increased a-syn expression is capable of triggering a parkinsonian syndrome in humans and PD-like pathology in animal models. Multiplication mutations of SNCA, the a-syn gene, that result in enhanced expression of the wild-type protein are causally associated with autosomal dominant parkinsonism. Increased protein levels promote self-assembly of a-syn, with formed proteinase-K resistant aggregate congeners and nitrated/phosphorylated forms mediating pathogenic effects. Administration of D- vs. H-PUFA as described in the previous examples reduces the accumulation of toxic a-syn in nigral cell bodies from MPTP-exposed mice, treated with D- vs. H-PUFA (FIG. 10). D-PUFA is a 1:1 mixture of D2-linolenic acid: D4-linolenic acid.

What is claimed is:

1. A method of treating a medical condition, comprising:
   selecting a subject that has ataxia or a neurodegenerative disease; and
   administering an effective amount of an isotopically modified polyunsaturated fatty acid or ester thereof to the subject;
   wherein the amount of isotope in the isotopically modified polyunsaturated fatty acid or ester thereof is above the naturally-occurring abundance level, wherein the amount of isotopically modified polyunsaturated fatty acid or ester thereof ingested by or administered to the subject is at least about 5% of the total amount of polyunsaturated fatty acid or ester thereof ingested by or administered to the subject, and wherein the isotopically modified polyunsaturated fatty acid or ester thereof is selected from the group consisting of 11, 11-D2-linoleic acid; 11-D-linoleic acid; 11, 11, 14, 14, D4-linolenic acid; 11,14, D2-linolenic acid; 11, 11, D2-linolenic acid; 11-D-linolenic acid; 14-D-linolenic acid; 14, 14, D2-linolenic acid, and ester thereof.

2. The method of claim 1,
   wherein the effective amount of the isotopically modified polyunsaturated fatty acid or ester is suitable for human consumption, and
   wherein the isotopically modified polyunsaturated fatty acid or ester thereof is capable of retaining its chemical identity when incorporated in a bodily constituent of the subject following ingestion or uptake by the subject, or is capable of conversion into higher homolog of the polyunsaturated fatty acid in the subject.

3. The method of claim 1, wherein the subject has a neurodegenerative disease.

4. The method of claim 1, wherein the isotopically modified polyunsaturated fatty acid or ester thereof has an isotopic purity at a modified position of from about 10% to 100%.

5. The method of claim 1, wherein the subject has a neurodegenerative disease associated with lipid peroxidation.

6. The method of claim 1, wherein
   the subject is administered a sufficient amount of an isotopically modified polyunsaturated fatty acid or ester thereof such that the subject maintains a sufficient concentration of isotopically modified polyunsaturated fatty acid to resist autooxidation.

7. The method of claim 1, wherein the subject has ataxia.

8. The method of claim 1, wherein the isotopically modified polyunsaturated fatty acid ester thereof is the ethyl or glyceryl ester of 11,11-D2-linoleic acid; 11-D-linoleic acid; 11-D-linoleic acid; 11,11,14,14-D4-linolenic acid; 11,14-D2-linolenic acid; 11,11-D2-linolenic acid; 11-D-linolenic acid; 14-D-linolenic acid; or 14,14-D2-linolenic acid.

9. The method of claim 1, wherein the isotopically modified polyunsaturated fatty acid ester thereof is the ethyl ester of 11,11-D2-linoleic acid; 11-D-linoleic acid; 11,11,14,14-D4-linolenic acid; 1,14-D2-linolenic acid; 11,11-D2-linolenic acid; 11-D-linolenic acid; 14-D-linolenic acid; or 14,14-D2-linolenic acid.

10. The method of claim 1, wherein the isotopically modified polyunsaturated fatty acid ester thereof is the ethyl ester of 11,11-D2-linoleic acid or 11-D-linoleic acid.

11. The method of claim 1, wherein the isotopically modified polyunsaturated fatty acid ester thereof is the ethyl ester of 11,11-D2-linoleic acid.

12. The method of claim 1, wherein the isotopically modified polyunsaturated fatty acid or ester thereof is a ω-6 polyunsaturated fatty acid.

13. The method of claim 1, wherein the isotopically modified polyunsaturated fatty acid or ester thereof is an ethyl ester.

14. A method of treating a medical condition, comprising selecting a subject having a neurodegenerative disease associated with lipid peroxidation or an ataxia; and
administering an effective amount of an isotopically modified polyunsaturated fatty acid or ester thereof or mixture thereof to the subject;
wherein the isotopically modified polyunsaturated fatty acid or ester thereof has a structure of formula (2)

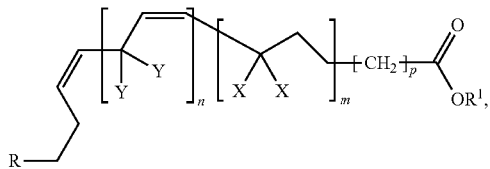

wherein:
R is H or $C_3H_7$,
$R^1$ is H or alkyl,
each Y is independently H or Deuterium with at least one Y being deuterium,
each X is independently H or Deuterium,
m=1-10,
n=1-5, and
p=1-10.

15. The method of claim 14, wherein the subject has an ataxia.

16. The method of claim 14, wherein the subject has a neurodegenerative disease associated with lipid peroxidation.

17. The method of claim 14, wherein the isotopically modified polyunsaturated fatty acid or ester thereof is a linoleic acid or ester thereof.

18. The method of claim 14, wherein the isotopically modified polyunsaturated fatty acid or ester thereof is a linolenic acid or ester thereof.

19. The method of claim 14, wherein the isotopically modified polyunsaturated fatty acid or ester thereof is an arachidonic acid or ester thereof.

20. The method of claim 14, wherein the isotopically modified polyunsaturated fatty acid or ester thereof is an eicosapentaenoic acid or ester thereof.

21. The method of claim 14, wherein the isotopically modified polyunsaturated fatty acid or ester thereof is a docosahexaenoic acid or ester thereof.

22. The method of claim 14, wherein the isotopically modified polyunsaturated fatty acid or ester thereof or mixture thereof is a mixture having two or more selected from the group consisting of linoleic acid or ester thereof, linolenic acid or ester thereof, arachidonic acid or ester thereof, eicosapentaenoic acid or ester thereof, and docosahexaenoic acid or ester thereof.

* * * * *